(12) United States Patent
Braun et al.

(10) Patent No.: US 8,822,378 B2
(45) Date of Patent: Sep. 2, 2014

(54) N-(TETRAZOL-5-YL)- AND N-(TRIAZOL-5-YL)ARYLCARBOXAMIDES AND USE THEREOF AS HERBICIDES

(75) Inventors: Ralf Braun, Ramberg (DE); Simon Dörner-Rieping, Neu-Anspach (DE); Arnim Köhn, Klein-Winternheim (DE); Hartmut Ahrens, Egelsbach (DE); Stefan Lehr, Lyons (FR); Andreas Van Almsick, Karben (DE); Isolde Häuser-Hahn, Leverkusen (DE); Hansjörg Dietrich, Liederbach am Taunus (DE); Elmar Gatzweiler, Bad Nauheim (DE); Ines Heinemann, Hofheim (DE); Christopher Hugh Rosinger, Hofheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/233,298

(22) PCT Filed: Jul. 30, 2012

(86) PCT No.: PCT/EP2012/064863
§ 371 (c)(1),
(2), (4) Date: Feb. 10, 2014

(87) PCT Pub. No.: WO2013/017559
PCT Pub. Date: Feb. 7, 2013

(65) Prior Publication Data
US 2014/0179527 A1      Jun. 26, 2014

(30) Foreign Application Priority Data
Aug. 3, 2011 (EP) .................................. 11176378

(51) Int. Cl.
| | | |
|---|---|---|
| *A01N 43/80* | (2006.01) | |
| *A01N 43/653* | (2006.01) | |
| *A01N 43/713* | (2006.01) | |
| *C07D 257/06* | (2006.01) | |
| *C07D 249/14* | (2006.01) | |
| *C07D 401/12* | (2006.01) | |

(52) U.S. Cl.
CPC ............. *A01N 43/80* (2013.01); *C07D 257/06* (2013.01); *A01N 43/713* (2013.01); *C07D 249/14* (2013.01); *C07D 401/12* (2013.01); *A01N 43/653* (2013.01)
USPC ........... 504/105; 504/261; 504/280; 504/272; 504/271; 504/112; 504/106; 548/251; 548/240; 548/265.4

(58) Field of Classification Search
None
See application file for complete search history.

(56) References Cited

U.S. PATENT DOCUMENTS

| | | |
|---|---|---|
| 5,013,659 A | 5/1991 | Bedbrook et al. |
| 5,500,367 A | 3/1996 | Hain et al. |
| 5,689,047 A | 11/1997 | Hain et al. |
| 5,834,268 A | 11/1998 | Hain et al. |
| 5,985,647 A | 11/1999 | Schroder et al. |
| 6,211,216 B1 | 4/2001 | Willms et al. |
| 6,376,429 B1 | 4/2002 | Van Almsick et al. |
| 2007/0244008 A1 | 10/2007 | Almsick et al. |

FOREIGN PATENT DOCUMENTS

| | | |
|---|---|---|
| EP | 0142924 A | 5/1985 |
| EP | 0193259 A1 | 9/1986 |
| EP | 0221044 A1 | 5/1987 |
| EP | 0242236 A1 | 10/1987 |
| EP | 0242246 A1 | 10/1987 |
| EP | 0257993 A2 | 3/1988 |
| EP | 309862 A1 | 4/1989 |
| EP | 0464461 A2 | 1/1992 |
| WO | 8402919 A1 | 8/1984 |
| WO | 9113972 A1 | 9/1991 |
| WO | 9119806 A1 | 12/1991 |
| WO | 9200377 A1 | 1/1992 |
| WO | 9211376 A1 | 7/1992 |
| WO | 9214827 A1 | 9/1992 |
| WO | 03010143 A1 | 2/2003 |
| WO | 03010153 A1 | 2/2003 |
| WO | 2004101532 A1 | 11/2004 |

OTHER PUBLICATIONS

International Search Report received in PCT/EP2012/064863 mailed Sep. 7, 2012.

*Primary Examiner* — Janet L Andres
*Assistant Examiner* — Timothy R Rozof
(74) *Attorney, Agent, or Firm* — Miles and Stockbridge

(57) ABSTRACT

N-(Tetrazol-5-yl)- and N-(triazol-5-yl)arylcarboxamides and use thereof as herbicides N-(Tetrazol-5-yl)- and N-(triazol-5-yl)arylcarboxamides of the general formula (I) are described as herbicides.

(I)

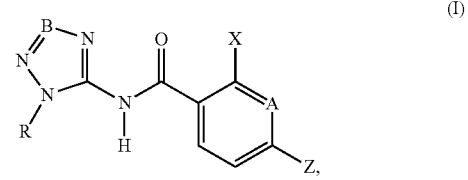

In this formula (I), X, Y, Z and R represent radicals such as hydrogen, organic radicals such as alkyl, and other radicals such as halogen. A and B represent N and CY.

15 Claims, No Drawings

N-(TETRAZOL-5-YL)- AND N-(TRIAZOL-5-YL)ARYLCARBOXAMIDES AND USE THEREOF AS HERBICIDES

CROSS REFERENCE TO RELATED APPLICATIONS

This application is a §371 National Stage Application of PCT/EP2012/064863, filed Jul. 30, 2012, which claims priority to EP 11176378.5 filed Aug. 3, 2011.

BACKGROUND

Field of the Invention

The invention relates to the technical field of the herbicides, in particular that of the herbicides for the selective control of broad-leaved weeds and weed grasses in crops of useful plants.

Description of Related Art

WO2003/010143 and WO2003/010153 disclose N-(tetrazol-5-yl)- and N-(triazol-5-yl)benzamides and their pharmacological action. EP101748937, earlier in priority but not prior-published, discloses certain N-(tetrazol-5-yl)- and N-(triazol-5-yl)benzamides and -nicotinamides as herbicides. It has now been found that N-(tetrazol-5-yl)- and N-(triazol-5-yl)arylcarboxamides and -nicotinamides carrying specific substituents in the 1-position of the tetrazole or triazole ring are particularly suitable as herbicides.

SUMMARY

Accordingly, the present invention provides N-(tetrazol-5-yl)- and N-(triazol-5-yl)arylcarboxamides of the formula (I) or salts thereof

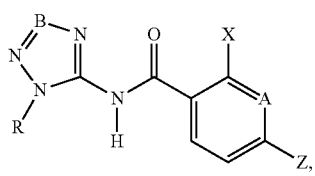

(I)

in which
A represents N or CY,
B represents N or CH,
X represents nitro, halogen, cyano, formyl, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_3\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO_2R^2$, $(C_1\text{-}C_6)$-alkyl-$CO_2R^1$, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $NR_1R_2$, $P(O)(OR^5)_2$, $CH_2P(O)(OR^5)_2$, $(C_1\text{-}C_6)$-alkyl-heteroaryl, $(C_1\text{-}C_6)$-alkyl-heterocyclyl, where the two last-mentioned radicals are each substituted by s radicals halogen, $(C_1\text{-}C_6)$-alkyl, halo-$(C_1\text{-}C_6)$-alkyl, $S(O)_n$—$(C_1\text{-}C_6)$-alkyl, $(C_1\text{-}C_6)$-alkoxy, halo-$(C_1\text{-}C_6)$-alkoxy, and where heterocyclyl carries n oxo groups, Y represents hydrogen, nitro, halogen, cyano, thiocyanato, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, $(C_3\text{-}C_6)$-cycloalkenyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$ $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO2R^2$, $(C_1\text{-}C_6)$-alkyl-$CO_2R^1$, $(C_1\text{-}C_6)$-alkyl-CN, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $N(R^1)_2$, $P(O)(OR^5)_2$, $CH_2P(O)(OR^5)_2$, $(C_1\text{-}C_6)$-alkyl-phenyl, $(C_1\text{-}C_6)$-alkyl-heteroaryl, $(C_1\text{-}C_6)$-alkyl-heterocyclyl, phenyl, heteroaryl or heterocyclyl, where the 6 last-mentioned radicals are each substituted by s radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $S(O)_n$—$(C_1\text{-}C_6)$-alkyl, $(C_1\text{-}C_6)$-alkoxy, halo-$(C_1\text{-}C_6)$-alkoxy, $(C_1\text{-}C_6)$-alkoxy-$(C_1\text{-}C_4)$-alkyl and cyanomethyl, and where heterocyclyl carries n oxo groups, Z represents halogen, cyano, thiocyanato, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1\text{-}C_6)$-alkyl-$S(O)_nR^2$, $(C_1\text{-}C_6)$-alkyl-$OR^1$, $(C_1\text{-}C_6)$-alkyl-$OCOR^1$, $(C_1\text{-}C_6)$-alkyl-$OSO_2R^2$, $(C_1\text{-}C_6)$-alkyl-$CO_2R^1$, $(C_1\text{-}C_6)$-alkyl-$SO_2OR^1$, $(C_1\text{-}C_6)$-alkyl-$CON(R^1)_2$, $(C_1\text{-}C_6)$-alkyl-$SO_2N(R^1)_2$, $(C_1\text{-}C_6)$-alkyl-$NR^1COR^1$, $(C_1\text{-}C_6)$-alkyl-$NR^1SO_2R^2$, $N(R^1)_2$, $P(O)(OR^5)_2$, heteroaryl, heterocyclyl or phenyl, where the three last-mentioned radicals are each substituted by s radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $S(O)_n$—$(C_1\text{-}C_6)$-alkyl, $(C_1\text{-}C_6)$-alkoxy and halo-$(C_1\text{-}C_6)$-alkoxy, and where heterocyclyl carries n oxo groups, or Z may also represent hydrogen, $(C_1\text{-}C_6)$-alkyl or $(C_1\text{-}C_6)$-alkoxy if Y represents the radical $S(O)_nR^2$, R represents $CH_2R^6$,
$CH_2$-heterocyclyl which is substituted by m oxo groups,
$(C_3\text{-}C_7)$-cycloalkyl which is substituted by t $(C_1\text{-}C_6)$-alkyl groups,
$(C_2\text{-}C_6)$-alkyl, $(C_3\text{-}C_7)$-cycloalkyl, halo-$(C_2\text{-}C_6)$-alkyl, $(C_2\text{-}C_6)$-alkenyl, halo-$(C_2\text{-}C_6)$-alkenyl, $(C_2\text{-}C_6)$-alkynyl or halo-$(C_2\text{-}C_6)$-alkynyl, each of which is substituted by u radicals from the group consisting of nitro, cyano, hydroxy, oxo, $SiR^5_3$, $PO(OR^6)_2$, $S(O)_n$—$(C_1\text{-}C_6)$-alkyl, $(C_1\text{-}C_6)$-alkoxy, halo-$(C_1\text{-}C_6)$-alkoxy, $N(R^3)_2$, $COR^3$, $OCOR^3$, $NR^3COR^3$, $NR^3SO_2R^4$, $(C_3\text{-}C_6)$-cycloalkyl, heteroaryl, heterocyclyl, phenyl, Q-heteroaryl, Q-heterocyclyl, Q-phenyl and Q-benzyl, where the radicals $(C_3\text{-}C_6)$-cycloalkyl, heteroaryl, heterocyclyl, phenyl, Q-heteroaryl, Q-heterocyclyl, Q-phenyl and Q-benzyl are each substituted by s substituents from the group consisting of methyl, ethyl, methoxy, cyano, nitro, trifluoromethyl and halogen, and where heterocyclyl and cycloalkyl carry n oxo groups, Q represents O, S or $NR^3$,
$R^1$ represents hydrogen, $(C_1\text{-}C_6)$-alkyl, $(C_1\text{-}C_6)$-haloalkyl, $(C_2\text{-}C_6)$-alkenyl, $(C_2\text{-}C_6)$-haloalkenyl, $(C_2\text{-}C_6)$-alkynyl, $(C_2\text{-}C_6)$-haloalkynyl, $(C_3\text{-}C_6)$-cycloalkyl, $(C_3\text{-}C_6)$-cycloalkenyl, $(C_3\text{-}C_6)$-halocycloalkyl, $(C_1\text{-}C_6)$-alkyl-O—$(C_1\text{-}C_6)$-alkyl, $(C_3\text{-}C_6)$-cycloalkyl-$(C_1\text{-}C_6)$-alkyl, phenyl, phenyl-$(C_1-C_6)$-alkyl, heteroaryl, $(C_1-C_6)$-alkyl-heteroaryl, heterocycl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-NR$^3$-heteroaryl, $(C_1-C_6)$-alkyl-NR$^3$-heterocyclyl, where the 21 last-mentioned radicals are substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and $(C_1-C_4)$-alkoxy-$(C_2-C_6)$-alkoxycarbonyl, and where heterocyclyl carries n oxo groups, R$^2$ represents $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-NR$^3$-heteroaryl, $(C_1-C_6)$-alkyl-NR$^3$-heterocyclyl, where the 21 last-mentioned radicals are substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and $(C_1-C_4)$-alkoxy-$(C_2-C_6)$-alkoxycarbonyl, and where heterocyclyl carries n oxo groups, R$^3$ represents hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, R$^4$ represents $(C_1-C_6)$-alkyl, $(C_2-C_6)$-alkenyl or $(C_2-C_6)$-alkynyl, $(C_3-C_6)$-cycloalkyl or $(C_3-C_6)$-cycloalkyl-$(C_1-C_6)$-alkyl, R$^5$ represents $(C_1-C_4)$-alkyl, R$^6$ represents OCOOR$^4$, NR$^4$COOR$^4$, S(O)$_n$—$(C_1-C_6)$-alkyl, S(O)$_n$—$(C_1-C_6)$-haloalkyl, nitro, cyano, SiR$^5{}_3$, PO(OR$^5$)$_2$, heterocyclyl or cycloalkyl, where the two last-mentioned radicals carry m oxo or hydroxy groups, m represents 1 or 2,
n represents 0, 1 or 2,
s represents 0, 1, 2 or 3,
t represents 1, 2, 3 or 4,
u represents 1, 2, 3, 4 or 5.

DETAILED DESCRIPTION OF A PREFERRED EMBODIMENT

In formula (I) and all the formulae below, alkyl radicals having more than two carbon atoms can be straight-chain or branched. Alkyl radicals are, for example, methyl, ethyl, n- or isopropyl, n-, iso-, t- or 2-butyl, pentyls, hexyls, such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. In each case, the multiple bond can be in any position of the unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond can be in any position.

Halogen represents fluorine, chlorine, bromine or iodine.

Heterocyclyl is a saturated, partially saturated or fully unsaturated cyclic radical which contains 3 to 6 ring atoms, 1 to 4 of which are from the group consisting of oxygen, nitrogen and sulfur, and which may additionally be fused to a benzo ring. Heterocyclyl is, for example, piperidinyl, pyrrolidinyl, tetrahydrofuranyl, dihydrofuranyl and oxetanyl. Heteroaryl is an aromatic cyclic radical which contains 3 to 6 ring atoms, 1 to 4 of which are from the group consisting of oxygen, nitrogen and sulfur, and which may additionally be fused to a benzo ring. Heteroaryl is, for example, benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

Where a group is substituted by a plurality of radicals, this means that this group is substituted by one or more identical or different representatives of the radicals mentioned.

Depending on the nature and the attachment of the substituents, the compounds of the formula (I) may be present as stereoisomers. If, for example, one or more asymmetrically substituted carbon atoms are present, there may be enantiomers and diastereomers. There may also be stereoisomers if n is 1 (sulfoxides). Stereoisomers may be obtained from the mixtures resulting from the preparation using customary separation methods, for example by chromatographic separation techniques. It is also possible to prepare stereoisomers selectively by using stereoselective reactions employing optically active starting materials and/or auxiliaries. The invention also relates to all stereoisomers and mixtures thereof embraced by the formula (I) but not specifically defined.

Preference is given to compounds of the formula (I) in which

A represents N or CY,

B represents N or CH,

X represents nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_1-C_6)$-alkyl-O-$(C_1-C_6)$-alkyl, $(C_3-C_6)$-cycloalkyl-$(C_1-C_6)$-alkyl, halo-$(C_3-C_6)$-cycloalkyl-$(C_1-C_6)$-alkyl, COR$^1$, OR$^1$, OCOR$^1$, OSO$_2$R$^2$, S(O)$_n$R$^2$, SO$_2$OR$^1$, SO$_2$N(R$^1$)$_2$, NR$^1$SO$_2$R$^2$, NR$^1$COR$^1$, $(C_1-C_6)$-alkyl-S(O)$_n$R$^2$, $(C_1-C_6)$-alkyl-OR$^1$, $(C_1-C_6)$-alkyl-OCOR$^1$, $(C_1-C_6)$-alkyl-OSO$_2$R$^2$, $(C_1-C_6)$-alkyl-CO$_2$R$^1$, $(C_1-C_6)$-alkyl-SO$_2$OR$^1$, $(C_1-C_6)$-alkyl-CON(R$^1$)$_2$, $(C_1-C_6)$-alkyl-SO$_2$N(R$^1$)$_2$, $(C_1-C_6)$-alkyl-NR$^1$COR$^1$ or $(C_1-C_6)$-alkyl-NR$^1$SO$_2$R$^2$, $(C_1-C_6)$-alkyl-heteroaryl, $(C_1-C_6)$-alkyl-heterocyclyl, where the two last-mentioned radicals are each substituted by s radicals halogen, $(C_1-C_6)$-alkyl, halo-$(C_1-C_6)$-alkyl, S(O)$_n$—$(C_1-C_6)$-alkyl, $(C_1-C_6)$-alkoxy, halo-$(C_1-C_6)$-alkoxy, and where heterocyclyl carries n oxo groups, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, COR$^1$, OR$^1$, COOR$^1$, OSO$_2$R$^2$, S(O)$_n$R$^2$, SO$_2$OR$^1$, SO$_2$N(R$^1$)$_2$, N(R$^1$)$_2$, NR$^1$SO$_2$R$^2$, NR$^1$COR$^1$, $(C_1-C_6)$-alkyl-S(O)$_n$R$^2$, $(C_1-C_6)$-alkyl-OR$^1$, $(C_1-C_6)$-alkyl-OCOR$^1$, $(C_1-C_6)$-alkyl-OSO$_2$R$^2$, $(C_1-C_6)$-alkyl-CO$_2$R$^1$, $(C_1-C_6)$-alkyl-SO$_2$OR$^1$, $(C_1-C_6)$-alkyl-CON(R$^1$)$_2$, $(C_1-C_6)$-alkyl-SO$_2$N(R$^1$)$_2$, $(C_1-C_6)$-alkyl-NR$^1$COR$^1$, $(C_1-C_6)$-alkyl-NR$^1$SO$_2$R$^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the 6 last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents halogen, cyano, thiocyanato, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $C(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, 1,2,4-triazol-1-yl, or Z may also represent hydrogen, $(C_1-C_6)$-alkyl or $(C_1-C_6)$-alkoxy if Y represents the radical $S(O)_nR^2$, R represents $CH_2R^6$,
$CH_2$-heterocyclyl which is substituted by m oxo groups,
$(C_2-C_6)$-alkyl, $(C_3-C_7)$-cycloalkyl, halo-$(C_2-C_6)$-alkyl, $(C_2-C_6)$-alkenyl, halo-$(C_2-C_6)$-alkenyl, $(C_2-C_6)$-alkynyl or halo-$(C_2-C_6)$-alkynyl, each of which is substituted by u radicals from the group consisting of nitro, cyano, hydroxy, oxo, $SiR^5_3$, $PO(OR^5)_2$, $S(O)_n$—$(C_1-C_6)$-alkyl, $(C_1-C_6)$-alkoxy, halo-$(C_1-C_6)$-alkoxy, $N(R^3)_2$, $COR^3$, $OCOR^3$, $NR^3COR^3$, $NR^3SO_2R^4$, $(C_3-C_6)$-cycloalkyl, heteroaryl, heterocyclyl, phenyl, Q-heteroaryl, Q-heterocyclyl, Q-phenyl and Q-benzyl, where the radicals $(C_3-C_6)$-cycloalkyl, heteroaryl, heterocyclyl, phenyl, Q-heteroaryl, Q-heterocyclyl, Q-phenyl and Q-benzyl are each substituted by s substituents from the group consisting of methyl, ethyl, methoxy, cyano, nitro, trifluoromethyl and halogen, and where heterocyclyl and cycloalkyl carry n oxo groups, Q represents O, S or $NR^3$, $R^1$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 last-mentioned radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries n oxo groups, $R^2$ represents $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where these radicals are substituted by s radicals from the group consisting of cyano, halogen, nitro, $OR^3$, $S(O) R^4$, $N(R^3)_2$, $NR^3OR^3$, $NR^3SO_2R^4$, $COR^3$, $OCOR^3$, $NR^3COR^3$, $CO_2R^3$, $CON(R^3)_2$ and $(C_1-C_4)$-alkoxy-$(C_2-C_6)$-alkoxycarbonyl, and where heterocyclyl carries n oxo groups, $R^3$ represents hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^4$ represents $(C_1-C_6)$-alkyl, $(C_2-C_6)$-alkenyl or $(C_2-C_6)$-alkynyl, $R^5$ represents methyl or ethyl, $R^6$ represents $OCOOR^4$, $NR^4COOR^4$, $S(O)_n$—$(C_1-C_6)$-alkyl, $S(O)_n$—$(C_1-C_6)$-haloalkyl, nitro, cyano, $SiR^5_3$, $PO(OR^5)_2$ or heterocyclyl which carries m oxo groups, m represents 1 or 2,
n represents 0, 1 or 2,
s represents 0, 1, 2 or 3,
u represents 1, 2, 3, 4 or 5.

Particular preference is given to compounds of the formula (I) in which

A represents N or CY,
B represents N or CH,
X represents nitro, halogen, cyano, $(C_1-C_6)$-alkyl, halo-$(C_1-C_6)$-alkyl, $(C_3-C_6)$-cycloalkyl, $OR^1$, $S(O)_nR^2$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-heteroaryl, $(C_1-C_6)$-alkyl-heterocyclyl, where the two last-mentioned radicals are each substituted by s radicals halogen, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy, and where heterocyclyl carries n oxo groups, Y represents hydrogen, nitro, halogen, cyano, $(C_1-C_6)$-alkyl, $(C_1-C_6)$-haloalkyl, $OR^1$, $S(O)_nR^2$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkyl-phenyl, $(C_1-C_6)$-alkyl-heteroaryl, $(C_1-C_6)$-alkyl-heterocyclyl, phenyl, heteroaryl or heterocyclyl, where the 6 last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents halogen, cyano, halo-$(C_1-C_6)$-alkyl, $(C_3-C_6)$-cycloalkyl, $S(O)_nR^2$, 1,2,4-triazol-1-yl, or Z may also represent hydrogen, methyl, methoxy or ethoxy if Y represents the radical $S(O)_nR^2$, R represents $CH_2R^6$,
$CH_2$-heterocyclyl, where heterocyclyl carries m oxo groups,
$(C_2-C_6)$-alkyl, $(C_3-C_7)$-cycloalkyl, halo-$(C_2-C_6)$-alkyl, $(C_2-C_6)$-alkenyl, halo-$(C_2-C_6)$-alkenyl, $(C_2-C_6)$-alkynyl or halo-$(C_2-C_6)$-alkynyl, each of which is substituted by u radicals from the group consisting of nitro, cyano, hydroxy, oxo, $SiR^5_3$, $PO(OR^5)_2$, $S(O)_n$—$(C_1-C_6)$-alkyl, $(C_1-C_6)$-alkoxy, halo-$(C_1-C_6)$-alkoxy, $N(R^3)_2$, $COR^3$, $OCOR^3$, $NR^3COR^3$, $NR^3SO_2R^4$, $(C_3-C_6)$-cycloalkyl, heteroaryl, heterocyclyl, phenyl, Q-heteroaryl, Q-heterocyclyl, Q-phenyl and Q-benzyl, where the radicals $(C_3-C_6)$-cycloalkyl, heteroaryl, heterocyclyl, phenyl, Q-heteroaryl, Q-heterocyclyl, Q-phenyl and Q-benzyl are each substituted by s substituents from the group consisting of methyl, ethyl, methoxy, cyano, nitro, trifluoromethyl and halogen, and where heterocyclyl and cycloalkyl carry n oxo groups, Q represents O, S or $NR^3$, $R^1$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 last-mentioned radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries n oxo groups, $R^2$ represents $(C_1-C_6)$-alkyl, $(C_3-C_6)$-cycloalkyl or $(C_3-C_6)$-cycloalkyl-$(C_1-C_6)$-alkyl, where the three radicals mentioned above are each substituted by s radicals from the group consisting of halogen and $OR^3$, $R^3$ represents hydrogen or $(C_1-C_6)$-alkyl, $R^4$ represents $(C_1-C_6)$-alkyl, $R^5$ represents methyl or ethyl, $R^6$ represents $OCOOR^4$, $NR^4COOR^4$, $S(O)_n-(C_1-C_6)$-alkyl, $S(O)_n-(C_1-C_6)$-haloalkyl, nitro, cyano, $SiR^5_3$, $PO(OR^5)_2$, m represents 1 or 2, n represents 0, 1 or 2, s represents 0, 1, 2 or 3, u represents 1, 2, 3, 4 or 5.

In all formulae given below, the substituents and symbols have, unless defined otherwise, the same meaning as described under formula (I).

Compounds according to the invention can be prepared, for example, by the method given in Scheme 1 by base-catalyzed reaction of a benzoyl chloride (II) with a 5-amino-1-H-1,2,4-triazole or 5-amino-1H-tetrazole (III):

Scheme 1

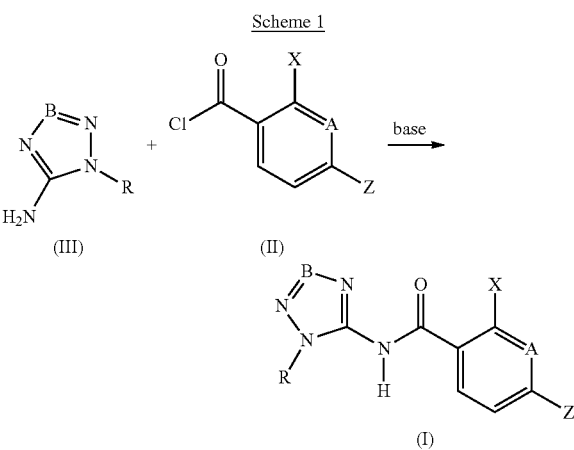

The benzoyl chlorides of the formula (II) or the benzoic acids on which they are based are known in principle and can be prepared, for example, according to the methods described in U.S. Pat. No. 6,376,429 B1, EP 1 585 742 A1 and EP 1 202 978 A1.

Compounds according to the invention can also be prepared by the method given in Scheme 2 by reacting a benzoic acid of the formula (IV) with a 5-amino-1-H-1,2,4-triazole or 5-amino-1H-tetrazole (III):

Scheme 2

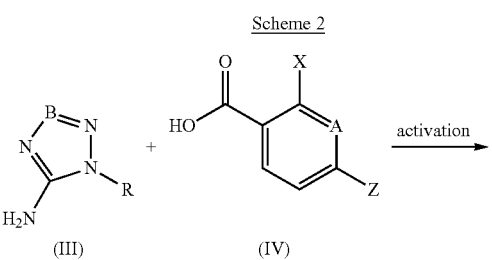

For the activation, use may be made of dehydrating agents usually employed for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P) etc.

Compounds according to the invention can also be prepared by the method given in Scheme 3 by reacting an N-(1H-1,2,4-triazol-5-yl)benzamide, N-(1H-tetrazol-5-yl)benzamide, N-(1H-1,2,4-triazol-5-yl)nicotinamide or N-(1H-tetrazol-5-yl)nicotinamide:

Scheme 3

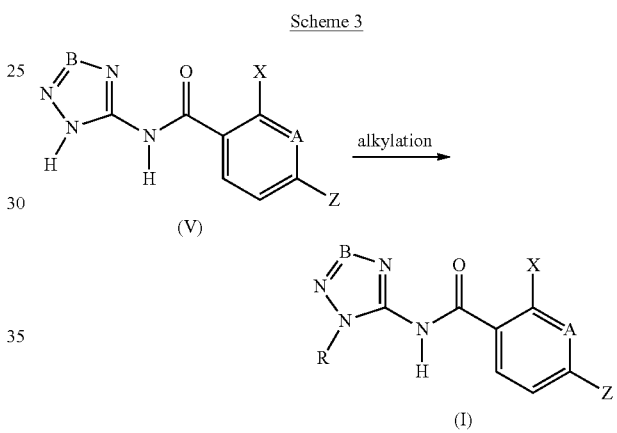

For the reaction given in Scheme 3, it is possible to use, for example, alkylating agents such as alkyl halides, alkylsulfonates or dialkyl sulfates in the presence of a base.

It may be expedient to change the order of reaction steps. Thus, benzoic acids carrying a sulfoxide can not be converted directly into their acid chlorides. Here, it is advisable to prepare initially, at the thioether stage, the amide and then to oxidize the thioether to the sulfoxide.

The 5-amino-1H-tetrazoles of the formula (III) can be prepared analogously to methods known from the literature. For example, 5-amino-1-R-tetrazoles can be prepared according to the method described in Journal of the American Chemical Society (1954), 76, 923-924 from aminotetrazole:

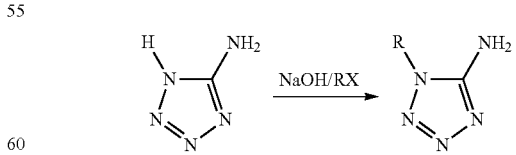

In the formula mentioned above, R represents, for example, an alkyl radical.

5-Amino-1-R-tetrazoles can be synthesized, for example, as described in Journal of the American Chemical Society (1954) 76, 88-89:

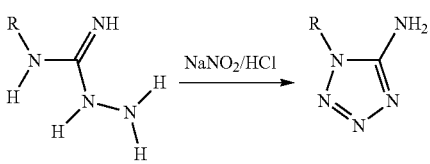

The 5-amino-1H-triazoles of the formula (III) can be prepared analogously to methods known from the literature. For example, 5-amino-1-R-triazoles can be prepared according to the method described in Zeitschrift für Chemie (1990), 30(12), 436-437 from aminotriazole:

5-Amino-1-R-triazoles can also be synthesized as described, for example, in Chemische Berichte (1964), 97(2), 396-404:

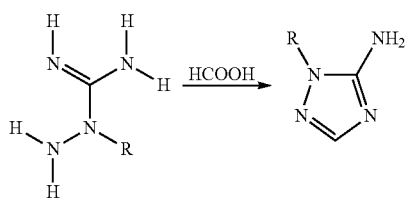

5-Amino-1-R-triazoles can also be synthesized as described, for example, in Angewandte Chemie (1963), 75, 918:

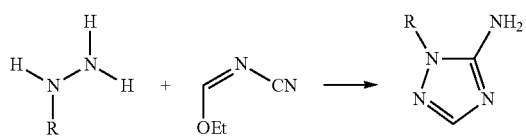

Collections of compounds of the formula (I) and/or salts thereof which can be synthesized by the aforementioned reactions can also be prepared in a parallel manner, it being possible for this to take place in a manual, partly automated or completely automated manner. In this connection, it is, for example, possible to automate the reaction procedure, the work-up or the purification of the products and/or intermediates. Overall, this is understood as meaning a procedure as described, for example, by D. Tiebes in Combinatorial Chemistry—Synthesis, Analysis, Screening (editor Günther Jung), Verlag Wiley 1999, on pages 1 to 34.

For the parallel reaction procedure and work-up, it is possible to use a series of commercially available instruments, for example Calpyso reaction blocks from Barnstead International, Dubuque, Iowa 52004-0797, USA or reaction stations from Radleys, Shirehill, Saffron Walden, Essex, CB 11 3AZ, England or MultiPROBE Automated Workstations from Perkin Elmer, Waltham, Mass. 02451, USA. For the parallel purification of compounds of the general formula (I) and salts thereof or of intermediates produced during the preparation, there are available, inter alia, chromatography apparatuses, for example from ISCO, Inc., 4700 Superior Street, Lincoln, Nebr. 68504, USA.

The apparatuses listed lead to a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Caliper, Hopkinton, Mass. 01748, USA.

The implementation of single or several synthesis steps can be supported through the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described here, the preparation of compounds of the general formula (I) and salts thereof can take place completely or partially by solid-phase supported methods. For this purpose, individual intermediates or all intermediates in the synthesis or a synthesis adapted for the corresponding procedure are bonded to a synthesis resin. Solid-phase supported synthesis methods are sufficiently described in the specialist literature, e.g. Barry A. Bunin in "The Combinatorial Index", Verlag Academic Press, 1998 and Combinatorial Chemistry—Synthesis, Analysis, Screening (editor Günther Jung), Verlag Wiley, 1999. The use of solid-phase supported synthesis methods permits a series of protocols known in the literature, which again can be carried out manually or in an automated manner. The reactions can be carried out, for example, by means of IRORI technology in microreactors from Nexus Biosystems, 12140 Community Road, Poway, Calif. 92064, USA.

Both on a solid phase and in liquid phase the procedure of individual or several synthesis steps can be supported through the use of microwave technology. The specialist literature describes a series of experimental protocols, for example in Microwaves in Organic and Medicinal Chemistry (editor C. O. Kappe and A. Stadler), Verlag Wiley, 2005.

The preparation according to the process described here produces compounds of the formula (I) and their salts in the form of substance collections which are called libraries. The present invention also provides libraries which comprise at least two compounds of the formula (I) and their salts.

The compounds of the formula (I) according to the invention (and/or their salts), hereinbelow also referred to together as "compounds according to the invention", have excellent herbicidal efficacy against a broad spectrum of economically important monocotyledonous and dicotyledonous annual harmful plants. The active compounds act efficiently even on perennial weeds which produce shoots from rhizomes, root stocks and other perennial organs and which are difficult to control.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum,* are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant-growth-regulatory properties, the active compounds can also be employed for controlling harmful plants in crops of genetically modified plants or plants modified by conventional mutagenesis. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storeability, composition and specific constituents. Thus, transgenic plants are known whose starch content is increased, or whose starch quality is altered, or those where the harvested material has a different fatty acid composition.

It is preferred, with respect to transgenic crops, to use the compounds according to the invention in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

It is preferred to use the compounds according to the invention or their salts in economically important transgenic crops of useful plants and ornamentals, for example of cereals such as wheat, barley, rye, oats, millet, rice, cassava and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example cotton, with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, nucleic acid molecules which allow mutagenesis or sequence changes by recombination of DNA sequences can be introduced into plasmids. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone" Genes and Clones, VCH Weinheim 2nd ed., 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product. To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds according to the invention in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes. These individual types of formulation are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N. J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyrdiethyl, cyprosulfamid, isoxadifen-ethyl, cloquintocet-mexyl and dichlormid.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To prepare the wettable powders, the herbicidally active compounds are ground finely, for example in customary apparatus such as hammer mills, blower mills and air-jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxideethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineers Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Formulations in the form of dusts comprise from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2009 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. Here, by way of example, one and in some cases a plurality of use forms are mentioned:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]-ethanesulfonamide, F-7967, i.e., 3-[7-chloro-5-fluoro-2-(trifluoromethyl)-1H-benzimidazol-4-yl]-1-methyl-6-(trifluoromethyl)pyrimidine-2,4(1H, 3H)dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e., O-(2,4-dimethyl-6-nitrophenyl)-O-ethyl-isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e., 1-(dimethoxyphosphoryl)-ethyl(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e., 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methylisothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron-ester, monuron, MT 128, i.e., 6-chloro-N-[(2E)-3-chloroprop-2-en-1-yl]-5-methyl-N-phenylpyridazin-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat-dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl-(2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e., 1-ethoxy-3-methyl-1-oxobut-3-en- 2-yl-5-[2-chloro-4-(trifluoromethyl)phenoxy]-2-nitrobenzoate, SYP-300, i.e., 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamon, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862 i.e. 3,4-dichloro-N-{2-[(4,6-dimethoxypyrimidin-2-yl)oxy]benzyl}aniline, and also the following compounds:

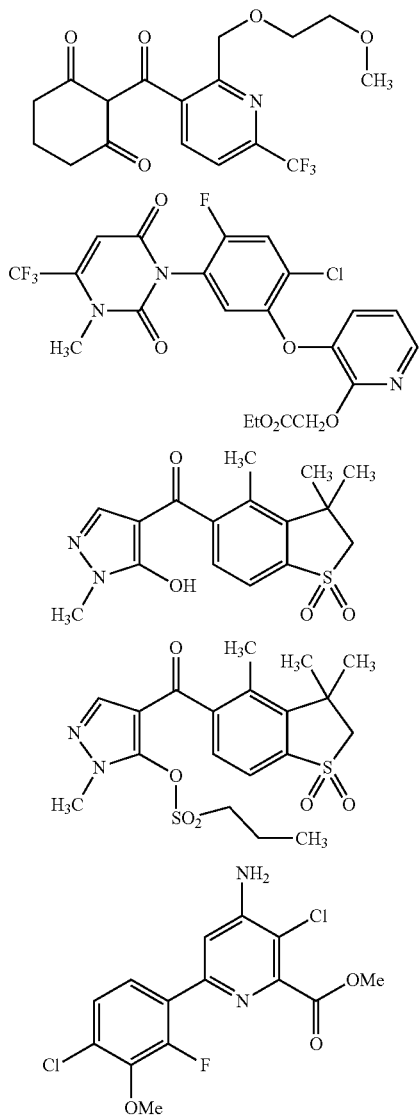

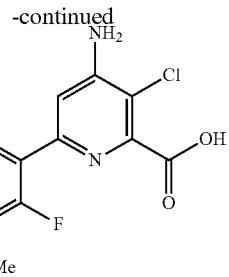

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted with other inert substances prior to application. The required application rate of the compounds of the formula (I) varies according to the external conditions such as, inter alia, temperature, humidity and the type of herbicide used. It may vary within wide limits, for example between 0.001 and 1.0 kg/ha or more of active substance; however, preferably it is between 0.005 and 750 g/ha.

The examples below illustrate the invention:

A. CHEMICAL EXAMPLES

1. Synthesis of 2-chloro-4-(methylsulfonyl)-N-(1-(2-methoxyethyl)tetrazol-5-yl)-benzamide, (Table Example No. 1-12)

176 mg (0.75 mmol) of 2-chloro-4-(methylsulfonyl)benzoyl chloride, 145 mg (1.0 mmol) of 5-amino-1-(2-methoxyethyl)tetrazole in 2 ml of pyridine are stirred at 60° C. for 12 h. 0.1 ml of water is then added, the mixture is stirred at 60° C. for 30 min and EA and 2N HCl are added. The organic phase is separated off and washed with 2N HCl and brine, dried over $Na_2SO_4$, concentrated and purified by RP—HPLC (acetonitrile/water). Yield 66 mg (23%).

Synthesis of 5-amino-1-(2-methoxyethyl)tetrazole

A mixture of 2.33 g (10 mmol) of S-methyl isothiosemicarbazide hydroiodide and 751 mg (10 mmol) of 2-methoxyethylamine in 10 ml of ethanol is heated under reflux until no more methyl mercaptan is released. The mixture is then substantially concentrated, and 10 ml of water, 0.3 ml of conc. nitric acid and 1.7 g (10 mmol) of silver nitrate in 2 ml of water are added successively with stirring. After 10 min of stirring, 0.5 ml of conc. hydrochloric acid is added, the precipitate is filtered off with suction and washed with 3 ml of water and 1.5 ml of conc. hydrochloric acid are added to the filtrate. At <5° C., 0.7 g (10 mmol) of sodium nitrite in 2 ml of water is then added to the mixture, and the pH is adjusted to 10 using 20% strength aqueous sodium hydroxide solution. The mixture is the heated to 60° C. for 30 min and, after cooling, extracted with ethyl acetate. The org. phase is washed 3× with sat. sodium chloride solution, dried and concentrated, and the residue is taken up in a little ethyl acetate and filtered. Beige crystals, yield 590 mg (40%). NMR (DMSO-$d_6$): 6.62 (brs, 2H), 4.26 (t, 2H), 3.65 (t, 2H), 3.23 (s, 3H)

TABLE 1

Compounds according to the invention of the formula (I) in which A represents CY, B represents N and R represents 2-methoxyethyl

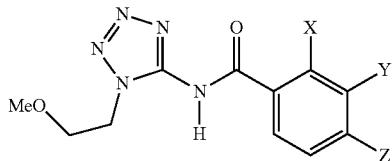

| No. | X | Y | Z | Physical data ($^1$H-NMR, DMSO-$d_6$, 400 MHz) |
|---|---|---|---|---|
| 1-1 | F | H | Cl | |
| 1-2 | F | H | Br | |
| 1-3 | F | H | SO$_2$Me | |
| 1-4 | F | H | SO$_2$Et | |
| 1-5 | F | H | CF$_3$ | |
| 1-6 | Cl | H | F | |
| 1-7 | Cl | H | Cl | 8.13 (s, 1H), 7.72 (d, 1H), 7.61 (dd, 1H), 4.55 (t, 2H), 3.78 (t, 2H), 3.22 (s, 3H) |
| 1-8 | Cl | H | Br | 9.90 (bs, 1H), 7.69-7.65 (m, 2H), 7.49 (dd, 1H), 4.63 (t, 2H), 3.83 (t, 2H), 3.36 (s, 3H) |
| 1-9 | Cl | H | I | 9.67 (bs, 1H), 7.85 (s, 1H), 7.77 (dd, 1H), 7.51 (d, 1H), 4.60 (t, 2H), 3.82 (t, 2H), 3.36 (s, 3H) |
| 1-10 | Cl | H | SMe | |
| 1-11 | Cl | H | SOMe | |
| 1-12 | Cl | H | SO$_2$Me | 8.04 (d, 1H), 7.98 (dd, 1H), 7.83 (s, 1H), 4.56 (t, 2H), 3.78 (t, 2H), 3.37 (s, 3H), 3.22 (s, 3H) |
| 1-13 | Cl | H | SO$_2$CH$_2$Cl | |
| 1-14 | Cl | H | SEt | |
| 1-15 | Cl | H | SO$_2$Et | |
| 1-16 | Cl | H | CF$_3$ | 9.84 (bs, 1H), 7.90 (d, 1H), 7.74 (s, 1H), 7.68 (d, 1H), 4.62 (t, 2H), 3.83 (t, 2H), 3.37 (s, 3H) |
| 1-17 | Cl | H | CN | |
| 1-18 | Cl | H | NMe$_2$ | |
| 1-19 | Cl | H | NHAc | |
| 1-20 | Cl | H | pyrrol-1-yl | |
| 1-21 | Cl | H | pyrrolidin-1-yl | |
| 1-22 | Cl | H | pyrazol-1-yl | |
| 1-23 | Cl | H | 1,2,4-triazol-1-yl | 9.62 (bs, 1H), 8.66 (s, 1H), 8.15 (s, 1H), 7.98 (d, 1H), 7.92 (s, 1H), 7.76 (d, 1H), 4.62 (t, 2H), 3.84 (t, 2H), 3.39 (s, 3H) |
| 1-24 | Cl | H | 4-methyl-3-trifluoromethyl-1,2,4-triazolin-5-on-1-yl | |
| 1-25 | Br | H | F | |
| 1-26 | Br | H | Cl | 9.79 (bs, 1H), 7.68-7.64 (m, 2H) 7.45 (dd, 1H), 4.63 (t, 2H), 3.83 (t, 2H), 3.36 (s, 3H) |
| 1-27 | Br | H | Br | |
| 1-28 | Br | H | SMe | 9.8 (bs, 1H), 7.65 (d, 1H), 7.45 (d, 1H), 7.26 (dd, 1H), 4.65 (t, 2H), 3.84 (t, 2H), 3.36 (s, 3H), 2.52 (s, 3H) |
| 1-29 | Br | H | SO$_2$Me | |
| 1-30 | Br | H | SO$_2$Et | |
| 1-31 | Br | H | CF$_3$ | |
| 1-32 | OMe | H | SO$_2$Me | |
| 1-33 | SMe | H | F | |
| 1-34 | SMe | H | Cl | 10.65 (bs, 1H), 7.83 (d, 1H), 7.31 (d, 1H), 7.28 (dd, 1H), 4.63 (t, 2H), 3.83 (t, 2H), 3.34 (s, 3H), 2.49 (s, 3H) |
| 1-35 | SO$_2$Me | H | Cl | |
| 1-36 | SMe | H | Br | |
| 1-37 | SO$_2$Me | H | Br | |
| 1-38 | SMe | H | SMe | |
| 1-39 | SO$_2$Me | H | SMe | |
| 1-40 | SO$_2$Me | H | SOMe | |
| 1-41 | SO$_2$Me | H | SO$_2$Me | |

TABLE 1-continued

Compounds according to the invention of the formula (I) in which A represents CY, B represents N and R represents 2-methoxyethyl

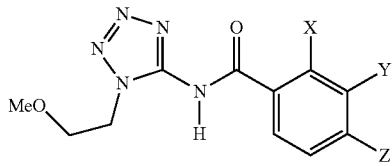

| No. | X | Y | Z | Physical data ($^1$H-NMR, DMSO-$d_6$, 400 MHz) |
|---|---|---|---|---|
| 1-42 | SMe | H | $CF_3$ | 10.6 (bs, 1H), 7.95 (d, 1H), 7.57 (s, 1H), 7.54 (d, 1H), 4.67 (t, 2H), 3.85 (t, 2H), 3.34 (s, 3H), 2.53 (s, 3H) |
| 1-43 | SOMe | H | $CF_3$ | |
| 1-44 | $SO_2$Me | H | $CF_3$ | 8.18 (s, 1H), 8.15 (d, 1H), 7.97 (d, 1H), 4.42 (m, 2H), 3.71 (m, 2H), 3.54 (s, 3H), 3.21 (s, 3H) |
| 1-45 | $SO_2$Et | H | Cl | |
| 1-46 | $SO_2$Et | H | Br | |
| 1-47 | $SO_2$Et | H | SMe | |
| 1-48 | $SO_2$Et | H | SOMe | |
| 1-49 | $SO_2$Et | H | $SO_2$Me | |
| 1-50 | $SO_2$Et | H | $CF_3$ | |
| 1-51 | $SO_2$NMePh | H | Cl | |
| 1-52 | $SO_2$NMe$_2$ | H | $CF_3$ | |
| 1-53 | $NO_2$ | H | F | |
| 1-54 | $NO_2$ | H | Cl | |
| 1-55 | $NO_2$ | H | Br | |
| 1-56 | $NO_2$ | H | I | |
| 1-57 | $NO_2$ | H | CN | |
| 1-58 | $NO_2$ | H | $SO_2$Me | |
| 1-59 | $NO_2$ | H | $SO_2$Et | |
| 1-60 | $NO_2$ | H | $CF_3$ | 10.3 (bs, 1H), 8.44 (s, 1H), 8.02 (d, 1H), 7.82 (d, 1H), 4.63 (t, 2H), 3.86 (t, 2H), 3.44 (s, 3H) |
| 1-61 | Me | H | F | |
| 1-62 | Me | H | $OCF_3$ | |
| 1-63 | Me | H | Cl | |
| 1-64 | Me | H | Br | |
| 1-65 | Me | H | $SO_2$Me | |
| 1-66 | Me | H | $SO_2CH_2$Cl | |
| 1-67 | Me | H | $SO_2$Et | |
| 1-68 | Me | H | $CF_3$ | |
| 1-69 | $CH_2$SMe | H | Br | 10.05 (bs, 1H), 7.58-7.52 (m, 3H), 4.65 (t, 2H), 3.96 (s, 2H), 3.83 (t, 2H), 3.34 (s, 3H), 2.05 (s, 3H) |
| 1-70 | $CH_2SO_2$Me | H | Br | 9.80 (bs, 1H), 7.72-7.68 (m, 2H), 7.59 (d, 1H), 4.74 (s, 2H), 4.62 (t, 2H), 3.81 (t, 2H), 3.35 (s, 3H), 2.98 (s, 3H) |
| 1-71 | $CH_2SO_2$Me | H | $CF_3$ | |
| 1-72 | Et | H | F | |
| 1-73 | Et | H | Cl | |
| 1-74 | Et | H | Br | |
| 1-75 | Et | H | $SO_2$Me | |
| 1-76 | Et | H | $SO_2CH_2$Cl | |
| 1-77 | Et | H | SEt | |
| 1-78 | Et | H | $SO_2$Et | |
| 1-79 | Et | H | $CF_3$ | |
| 1-80 | $CF_3$ | H | Cl | 10.05 (bs, 1H), 7.76 (s, 1H), 7.70 (d, 1H), 7.67 (d, 1H), 4.61 (t, 2H), 3.82 (t, 2H), 3.33 (s, 3H) |
| 1-81 | $CF_3$ | H | Br | |
| 1-82 | $CF_3$ | H | $SO_2$Me | |
| 1-83 | $CF_3$ | H | $SO_2$NMe$_2$ | 10.5 (bs, 1H), 8.14 (s, 1H), 8.08 (d, 1H), 7.89 (d, 1H), 4.63 (t, 2H), 3.81 (t, 2H), 3.34 (s, 3H), 2.80 (s, 6H) |
| 1-84 | $CF_3$ | H | $CF_3$ | |
| 1-85 | $NO_2$ | $NH_2$ | F | |
| 1-86 | $NO_2$ | NHMe | F | |
| 1-87 | $NO_2$ | $NMe_2$ | F | |
| 1-88 | $NO_2$ | Me | Cl | |

TABLE 1-continued

Compounds according to the invention of the formula (I) in which A represents CY, B represents N and R represents 2-methoxyethyl

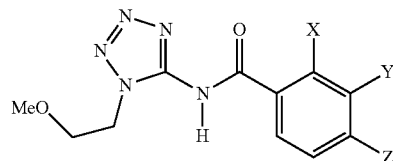

| No. | X | Y | Z | Physical data ($^1$H-NMR, DMSO-$d_6$, 400 MHz) |
|---|---|---|---|---|
| 1-89 | NO$_2$ | NH$_2$ | Cl | |
| 1-90 | NO$_2$ | NHMe | Cl | |
| 1-91 | NO$_2$ | NMe$_2$ | Cl | |
| 1-92 | NO$_2$ | NH$_2$ | Br | |
| 1-93 | NO$_2$ | NHMe | Br | |
| 1-94 | NO$_2$ | NMe$_2$ | Br | |
| 1-95 | NO$_2$ | NH$_2$ | CF$_3$ | |
| 1-96 | NO$_2$ | NMe$_2$ | CF$_3$ | |
| 1-97 | NO$_2$ | NH$_2$ | SO$_2$Me | |
| 1-98 | NO$_2$ | NH$_2$ | SO$_2$Et | |
| 1-99 | NO$_2$ | NHMe | SO$_2$Me | |
| 1-100 | NO$_2$ | NMe$_2$ | SO$_2$Me | |
| 1-101 | NO$_2$ | NMe$_2$ | SO$_2$Et | |
| 1-102 | NO$_2$ | NH$_2$ | 1H-1,2,4-triazol-1-yl | |
| 1-103 | NO$_2$ | NHMe | 1H-1,2,4-triazol-1-yl | |
| 1-104 | NO$_2$ | NMe$_2$ | 1H-1,2,4-triazol-1-yl | |
| 1-105 | Me | SMe | H | |
| 1-106 | Me | SOMe | H | |
| 1-107 | Me | SO$_2$Me | H | |
| 1-108 | Me | SEt | H | |
| 1-109 | Me | SOEt | H | |
| 1-110 | Me | SO$_2$Et | H | |
| 1-111 | Me | S(CH$_2$)$_2$OMe | H | |
| 1-112 | Me | SO(CH$_2$)$_2$OMe | H | |
| 1-113 | Me | SO$_2$(CH$_2$)$_2$OMe | H | |
| 1-114 | Me | F | F | |
| 1-115 | Me | SEt | F | |
| 1-116 | Me | SOEt | F | |
| 1-117 | Me | SO$_2$Et | F | |
| 1-118 | Me | Me | Cl | 9.75 (brs, 1H), 7.35 (d, 1H), 7.34 (d, 1H), 4.62 (t, 2H), 3.82 (t, 2H), 3.34 (s, 3H), 2.46 (s, 3H), 2.40 (s, 3H) |
| 1-119 | Me | NH$_2$ | Cl | |
| 1-120 | Me | NHMe | Cl | |
| 1-121 | Me | NMe$_2$ | Cl | |
| 1-122 | Me | O(CH$_2$)$_2$OMe | Cl | |
| 1-123 | Me | O(CH$_2$)$_3$OMe | Cl | 9.84 (bs, 1H), 7.35 (d, 1H), 7.32 (d, 1H), 4.62 (t, 2H), 4.00 (t, 2H), 3.83 (t, 2H), 3.64 (t, 2H), 3.38 (s, 3H), 3.35 (s, 3H), 2.49 (s, 3H), 2.11 (m, 2H) |
| 1-124 | Me | O(CH$_2$)$_4$OMe | Cl | |
| 1-125 | Me | O(CH$_2$)$_2$SMe | Cl | 11.45 (bs, 1H), 7.51 (d, 1H), 7.39 (d, 1H), 4.54 (t, 2H), 4.07 (t, 2H), 3.75 (t, 2H), 3.22 (s, 3H), 2.92 (t, 2H), 2.40 (s, 3H), 2.16 (s, 3H) |
| 1-126 | Me | O(CH$_2$)$_2$SEt | Cl | |
| 1-127 | Me | O(CH$_2$)$_3$SMe | Cl | |
| 1-128 | Me | OCH$_2$CONMe$_2$ | Cl | 10.27 (brs, 1H), 7.39 (d, H), 7.32 (d, 1H), 4.63 (t, 2H), 4.60 (s, 2H), 3.84 (t, 2H), 3.35 (s, 3H), 3.06 (s, 3H), 3.01 (s, 3H), 2.41 (s, 3H) |
| 1-129 | Me | O(CH$_2$)$_2$CONMe$_2$ | Cl | |
| 1-130 | Me | O(CH$_2$)$_2$—NH(CO)NMe$_2$ | Cl | |
| 1-131 | Me | O(CH$_2$)$_2$NH(CO)NHCO$_2$Et | Cl | |
| 1-132 | Me | O(CH$_2$)$_2$NHCO$_2$Me | Cl | |
| 1-133 | Me | OCH$_2$NHSO$_2$cPr | Cl | |
| 1-134 | Me | O(CH$_2$)-5-(2,4-dimethyl-2,4-dihydro)-3H-1,2,4-triazol-3-one | Cl | |

TABLE 1-continued

Compounds according to the invention of the formula (I) in which A represents CY, B represents N and R represents 2-methoxyethyl

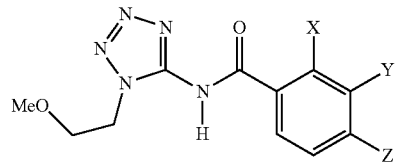

| No. | X | Y | Z | Physical data ($^1$H-NMR, DMSO-$d_6$, 400 MHz) |
|---|---|---|---|---|
| 1-135 | Me | O(CH$_2$)-3,5-dimethyl-1,2-oxazol-4-yl | Cl | |
| 1-136 | Me | F | Cl | |
| 1-137 | Me | Cl | Cl | |
| 1-138 | Me | SMe | Cl | |
| 1-139 | Me | SOMe | Cl | |
| 1-140 | Me | SO$_2$Me | Cl | |
| 1-141 | Me | SEt | Cl | |
| 1-142 | Me | SOEt | Cl | |
| 1-143 | Me | SO$_2$Et | Cl | |
| 1-144 | Me | S(CH$_2$)$_2$OMe | Cl | |
| 1-145 | Me | SO(CH$_2$)$_2$OMe | Cl | |
| 1-146 | Me | SO$_2$(CH$_2$)$_2$OMe | Cl | |
| 1-147 | Me | NH$_2$ | Br | |
| 1-148 | Me | NHMe | Br | |
| 1-149 | Me | NMe$_2$ | Br | |
| 1-150 | Me | OMe | Br | 9.94 (bs, 1H), 7.53 (d, 1H), 7.27 (d, 1H), 4.62 (t, 2H), 3.85 (s, 3H), 3.83 (t, 2H), 3.34 (s, 3H), 3.22 (s, 3H), 2.51 (s, 3H) |
| 1-151 | Me | OEt | Br | |
| 1-152 | Me | O(CH$_2$)$_2$OMe | Br | 9.86 (bs, 1H), 7.52 (d, 1H), 7.25 (d, 1H), 4.62 (t, 2H), 4.10 (t, 2H), 3.84-3.78 (m, 4H), 3.47 (s, 3H), 3.36 (s, 3H), 2.53 (s, 3H) |
| 1-153 | Me | O(CH$_2$)$_3$OMe | Br | 9.81 (bs, 1H), 7.52 (d, 1H), 7.24 (d, 1H), 4.61 (t, 2H), 4.01 (t, 2H), 3.83 (t, 2H), 3.65 (t, 2H), 3.38 (s, 3H), 3.35 (s, 3H), 2.50 (s, 3H), 2.13 (m, 2H) |
| 1-154 | Me | O(CH$_2$)$_2$SMe | Br | 11.46 (bs, 1H), 7.65 (d, 1H), 7.32 (d, 1H), 4.54 (t, 2H), 4.05 (t, 2H), 3.75 (t, 2H), 3.22 (s, 3H), 2.93 (t, 2H), 2.41 (s, 3H), 2.17 (s, 3H) |
| 1-155 | Me | O(CH$_2$)$_2$SEt | Br | 11.45 (bs, 1H), 7.65 (d, 1H), 7.32 (d, 1H), 4.54 (t, 2H), 4.03 (t, 2H), 3.75 (t, 2H), 3.22 (s, 3H), 2.96 (t, 2H), 2.63 (q, 2H), 2.41 (s, 3H), 1.22 (t, 3H) |
| 1-156 | Me | O(CH$_2$)$_3$SMe | Br | |
| 1-157 | Me | OCH$_2$CONMe$_2$ | Br | 10.32 (bs, 1H), 7.49 (d, 1H), 7.32 (d, 1H), 4.62 (t, 2H), 4.57 (s, 2H), 3.83 (t, 2H), 3.35 (s, 3H), 3.05 (s, 3H), 3.01 (s, 3H), 2.38 (s, 3H) |
| 1-158 | Me | O(CH$_2$)-5-pyrrolidin-2-one | Br | |
| 1-159 | Me | SMe | Br | |
| 1-160 | Me | SOMe | Br | |
| 1-161 | Me | SO$_2$Me | Br | |
| 1-162 | Me | SEt | Br | 9.22 (bs, 1H), 7.64 (d, 1H), 7.28 (d, 1H), 4.60 (t, 2H), 3.82 (t, 2H), 3.35 (s, 3H), 2.88 (q, 2H), 2.79 (s, 3H), 1.24 (t, 3H) |
| 1-163 | Me | SOEt | Br | 9.60 (bs, 1H), 7.56 (d, 1H), 7.41 (d, 1H), 4.60 (t, 2H), 3.82 (t, 2H), 3.35 (s, 3H), 3.29-3.34 (m, 1H), 3.10-3.15 (m, 1H), 2.82 (s, 3H), 1.42 (t, 3H) |
| 1-164 | Me | SO$_2$Et | Br | 9.38 (bs, 1H), 7.78 (d, 1H), 7.46 (bs, 1H), 4.60 (t, 2H), 3.82 (t, 2H), 3.50 (q, 2H), 3.37 (s, 3H), 2.85 (s, 3H), 1.39 (t, 3H) |
| 1-165 | Me | SMe | I | |
| 1-166 | Me | SOMe | I | |
| 1-167 | Me | SO$_2$Me | I | |
| 1-168 | Me | SEt | I | |

TABLE 1-continued

Compounds according to the invention of the formula (I) in which A represents CY, B represents N and R represents 2-methoxyethyl

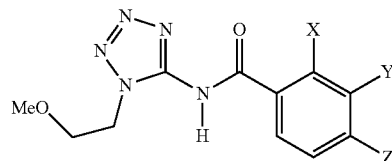

| No. | X | Y | Z | Physical data ($^1$H-NMR, DMSO-$d_6$, 400 MHz) |
|---|---|---|---|---|
| 1-169 | Me | SOEt | I | |
| 1-170 | Me | SO$_2$Et | I | |
| 1-171 | Me | Cl | CF$_3$ | 9.95 (brs, 1H), 7.68 (d, H), 7.56 (d, 1H), 4.64 (t, 2H), 3.83 (t, 2H), 3.36 (s, 3H), 2.59 (s, 3H) |
| 1-172 | Me | SMe | CF$_3$ | 7.74 (d, H), 7.68 (d, 1H), 4.48 (m, 2H), 3.74 (m, 2H), 3.22 (s, 3H), 2.70 (s, 3H), 2.30 (s, 3H) |
| 1-173 | Me | SOMe | CF$_3$ | 7.90 (s, 2H), 4.59 (t, 2H), 3.76 (t, 2H), 3.24 (s, 3H), 3.06 (s, 3H), 2.88 (s, 3H) |
| 1-174 | Me | SO$_2$Me | CF$_3$ | 7.89 (d, 1H), 7.82 (d, 1H), 4.37 (m, 2H), 3.71 (m, 2H), 3.37 (s, 3H), 3.22 (s, 3H), 2.75 (s, 3H) |
| 1-175 | Me | SEt | CF$_3$ | |
| 1-176 | Me | SOEt | CF$_3$ | |
| 1-177 | Me | SO$_2$Et | CF$_3$ | |
| 1-178 | Me | S(CH$_2$)$_2$OMe | CF$_3$ | |
| 1-179 | Me | S(O)(CH$_2$)$_2$OMe | CF$_3$ | |
| 1-180 | Me | SO$_2$(CH$_2$)$_2$OMe | CF$_3$ | |
| 1-181 | Me | SMe | OMe | |
| 1-182 | Me | SOMe | OMe | |
| 1-183 | Me | SO$_2$Me | OMe | |
| 1-184 | Me | SEt | OMe | |
| 1-185 | Me | SOEt | OMe | |
| 1-186 | Me | SO$_2$Et | OMe | |
| 1-187 | Me | Me | SMe | 9.75 (brs, 1H), 7.45 (d, 1H), 7.08 (d, 1H), 4.63 (t, 2H), 3.83 (t, 2H), 3.35 (s, 1H), 2.50 (s, 3H), 2.46 (s, 3H), 2.32 (s, 3H) |
| 1-188 | Me | Me | SO$_2$Me | 9.90 (brs, 1H), 8.02 (d, 1H), 7.51 (d, 1H), 4.64 (t, 2H), 3.83 (t, 2H), 3.35 (s, 1H), 3.13 (s, 3H), 2.70 (s, 3H), 2.48 (s, 3H) |
| 1-189 | Me | Me | SEt | |
| 1-190 | Me | Me | SO$_2$Et | |
| 1-191 | Me | 4,5-dihydro-1,2-oxazol-3-yl | SO$_2$Me | |
| 1-192 | Me | 4,5-dihydro-1,2-oxazol-3-yl | SO$_2$Et | |
| 1-193 | Me | 5-cyanomethyl-4,5-dihydro-1,2-oxazol-3-yl | SO$_2$Me | |
| 1-194 | Me | 5-cyanomethyl-4,5-dihydro-1,2-oxazol-3-yl | SO$_2$Et | |
| 1-195 | Me | NH$_2$ | SO$_2$Me | |
| 1-196 | Me | NHMe | SO$_2$Me | |
| 1-197 | Me | NMe$_2$ | SO$_2$Me | 9.95 (brs, 1H), 7.99 (d, 1H), 7.51 (d, 1H), 4.64 (t, 2H), 3.84 (t, 2H), 3.37 (s, 1H), 3.27 (s, 3H), 2.92 (s, 6H), 2.50 (s, 3H) |
| 1-198 | Me | NHEt | SO$_2$Me | |
| 1-199 | Me | NHnPr | SO$_2$Me | |
| 1-200 | Me | NHiPr | SO$_2$Me | 9.87 (brs, 1H), 7.80 (d, 1H), 7.12 (d, 1H), 4.64 (t, 2H), 3.83 (t, 2H), 3.77 (sept, 1H), 3.36 (s, 1H), 3.11 (s, 3H), 2.41 (s, 3H), 1.22 (d, 6H) |
| 1-201 | Me | NHcPr | SO$_2$Me | 9.71 (brs, 1H), 7.75 (d, 1H), 7.06 (d, 1H), 6.25 (bs, 1H), 4.64 (t, 2H), 3.83 (t, 2H), 3.36 (s, 1H), 3.00 (s, 3H), 2.84 (m, 1H), 2.60 (s, 3H), 0.81 (m, 2H), 0.61 (m, 2H) |
| 1-202 | Me | NHiBu | SO$_2$Me | |
| 1-203 | Me | NHCH$_2$cPr | SO$_2$Me | |

TABLE 1-continued

Compounds according to the invention of the formula (I) in which A
represents CY, B represents N and R represents 2-methoxyethyl

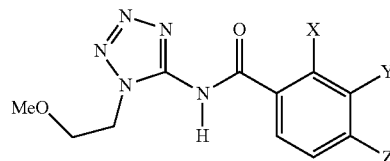

| No. | X | Y | Z | Physical data ($^1$H-NMR, DMSO-$d_6$, 400 MHz) |
|---|---|---|---|---|
| 1-204 | Me | NH(CH$_2$)$_2$OMe | SO$_2$Me | 9.95 (bs, 1H), 7.81 (d, 1H), 7.15 (d, 1H), 4.64 (t, 2H), 3.84 (t, 2H), 3.60 (t, 2H), 3.42 (t, 2H), 3.40 (s, 3H), 3.36 (s, 3H), 3.20 (s, 3H), 2.43 (s, 3H) |
| 1-205 | Me | NH(CH$_2$)$_2$OEt | SO$_2$Me | |
| 1-206 | Me | NH(CH$_2$)$_3$OMe | SO$_2$Me | |
| 1-207 | Me | NHCH$_2$CH(OMe)Me | SO$_2$Me | |
| 1-208 | Me | NHCH$_2$CH(OMe)CH$_2$OMe | SO$_2$Me | |
| 1-209 | Me | NH(CH$_2$)$_3$OEt | SO$_2$Me | |
| 1-210 | Me | NHCH$_2$-tetrahydrofuran-2-yl | SO$_2$Me | 9.91 (bs, 1H), 7.81 (d, 1H), 7.15 (d, 1H), 4.64 (t, 2H), 4.15 (m, 1H), 3.91 (dd, 1H), 3.84 (t, 2H), 3.79 (dd, 1H), 3.43 (dd, 1H), 3.36 (s, 3H), 3.24 (s, 3H), 3.18 (dd, 1H), 2.43 (s, 3H), 2.09-1.90 (m, 3H), 1.72-1.63 (m, 1H) |
| 1-211 | Me | NHCH$_2$-(4-Me-[1,3]dioxolan-2-yl) | SO$_2$Me | |
| 1-212 | Me | NH(CH$_2$)$_2$-(4-Me-[1,3]dioxolan-2-yl) | SO$_2$Me | |
| 1-213 | Me | NHCH$_2$-[1,3]dioxan-2-yl | SO$_2$Me | |
| 1-214 | Me | NHCH$_2$CONHEt | SO$_2$Me | |
| 1-215 | Me | pyrazol-1-yl | SO$_2$Me | 11.80 (brs, 1H), 8.11 (d, 1H), 8.01 (d, 1H), 7.99 (d, 1H), 7.88 (d, 1H), 6.59 (t, 1H), 4.58 (t, 2H), 3.77 (t, 2H), 3.22 (s, 3H), 3.05 (s, 3H), 1.90 (s, 3H) |
| 1-216 | Me | 3,5-Me$_2$-pyrazol-1-yl | SO$_2$Me | |
| 1-217 | Me | 1,2,3-triazol-1-yl | SO$_2$Me | |
| 1-218 | Me | 1,2,4-triazol-1-yl | SO$_2$Me | |
| 1-219 | Me | OH | SO$_2$Me | |
| 1-220 | Me | OMe | SO$_2$Me | 10.2 (brs, 1H), 7.91 (d, 1H), 7.50 (d, 1H), 4.65 (t, 2H), 3.98 (s, 1H), 3.84 (t, 2H), 3.37 (s, 3H), 3.26 (s, 3H), 2.53 (s, 3H) |
| 1-221 | Me | OMe | SO$_2$Et | |
| 1-222 | Me | OEt | SO$_2$Me | |
| 1-223 | Me | OEt | SO$_2$Et | |
| 1-224 | Me | OiPr | SO$_2$Me | |
| 1-225 | Me | OiPr | SO$_2$Et | |
| 1-226 | Me | O(CH$_2$)$_2$OMe | SO$_2$Me | |
| 1-227 | Me | O(CH$_2$)$_2$OMe | SO$_2$Et | |
| 1-228 | Me | O(CH$_2$)$_3$OMe | SO$_2$Me | |
| 1-229 | Me | O(CH$_2$)$_3$OMe | SO$_2$Et | |
| 1-230 | Me | O(CH$_2$)$_4$OMe | SO$_2$Me | |
| 1-231 | Me | O(CH$_2$)$_4$OMe | SO$_2$Et | |
| 1-232 | Me | O(CH$_2$)$_2$SMe | SO$_2$Me | |
| 1-233 | Me | O(CH$_2$)$_2$SEt | SO$_2$Me | |
| 1-234 | Me | O(CH$_2$)$_3$SMe | SO$_2$Me | |
| 1-235 | Me | O(CH$_2$)$_2$NHSO2Me | SO$_2$Me | |
| 1-236 | Me | O(CH$_2$)$_2$NHSO2Me | SO$_2$Et | |
| 1-237 | Me | OCH$_2$(CO)NMe$_2$ | SO$_2$Me | 10.5 (brs, 1H), 7.94 (d, 1H), 7.55 (d, 1H), 4.82 (s, 2H), 4.67 (t, 2H), 3.83 (t, 2H), 3.40 (s, 3H), 3.36 (s, 3H), 3.04 (s, 3H), 2.95 (s, 3H), 2.53 (s, 3H) |
| 1-238 | Me | OCH$_2$(CO)NMe$_2$ | SO$_2$Et | |
| 1-239 | Me | OCH$_2$-tetrahydrofuran-2-yl | SO$_2$Me | |
| 1-240 | Me | OCH$_2$-tetrahydrofuran-2-yl | SO$_2$Et | |
| 1-241 | Me | [1,4]dioxan-2-ylmethoxy | SO$_2$Me | |
| 1-242 | Me | [1,4]dioxan-2-ylmethoxy | SO$_2$Et | |
| 1-243 | Me | F | SMe | |
| 1-244 | Me | F | SO$_2$Me | |

TABLE 1-continued

Compounds according to the invention of the formula (I) in which A represents CY, B represents N and R represents 2-methoxyethyl

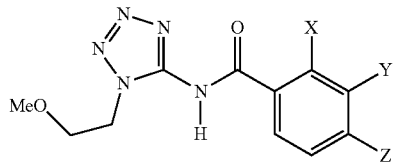

| No. | X | Y | Z | Physical data ($^1$H-NMR, DMSO-$d_6$, 400 MHz) |
|---|---|---|---|---|
| 1-245 | Me | Cl | SO$_2$Me | 10.05 (brs, 1H), 8.11 (d, H), 7.61 (d, 1H), 4.64 (t, 2H), 3.84 (t, 2H), 3.36 (s, 3H), 3.32 (s, 3H), 2.61 (s, 3H) |
| 1-246 | Me | SMe | SO$_2$Me | 7.99 (d, 1H), 7.74 (d, 1H), 4.49 (t, 2H), 3.74 (t, 2H), 3.52 (s, 3H), 3.23 (s, 3H), 2.69 (s, 3H), 2.38 (s, 3H) |
| 1-247 | Me | SOMe | SO$_2$Me | |
| 1-248 | Me | SO$_2$Me | SO$_2$Me | 11.80 (brs, 1H), 8.28 (d, 1H), 8.08 (d, 1H), 4.59 (t, 2H), 3.77 (t, 2H), 3.60 (s, 1H), 3.58 (s, 3H), 3.23 (s, 3H), 2.72 (s, 3H) |
| 1-249 | Me | SO$_2$Me | SO$_2$Et | |
| 1-250 | Me | SEt | SO$_2$Me | |
| 1-251 | Me | SOEt | SO$_2$Me | |
| 1-252 | Me | SO$_2$Et | SO$_2$Me | |
| 1-253 | Me | S(CH$_2$)$_2$OMe | SO$_2$Me | |
| 1-254 | Me | SO(CH$_2$)$_2$OMe | SO$_2$Me | |
| 1-255 | Me | SO$_2$(CH$_2$)$_2$OMe | SO$_2$Me | |
| 1-256 | CH$_2$SMe | OMe | SO$_2$Me | |
| 1-257 | CH$_2$OMe | OMe | SO$_2$Me | |
| 1-258 | CH$_2$O(CH$_2$)$_2$OMe | NH(CH$_2$)$_2$OEt | SO$_2$Me | |
| 1-259 | CH$_2$O(CH$_2$)$_2$OMe | NH(CH$_2$)$_3$OEt | SO$_2$Me | |
| 1-260 | CH$_2$O(CH$_2$)$_3$OMe | OMe | SO$_2$Me | |
| 1-261 | CH$_2$O(CH$_2$)$_2$OMe | NH(CH$_2$)$_2$OMe | SO$_2$Me | |
| 1-262 | CH$_2$O(CH$_2$)$_2$OMe | NH(CH$_2$)$_3$OMe | SO$_2$Me | |
| 1-263 | Et | NH(CH$_2$)$_2$OMe | SO$_2$Me | |
| 1-264 | Et | OMe | SO$_2$Me | |
| 1-265 | Et | OMe | SO$_2$Et | |
| 1-266 | Et | OEt | SO$_2$Me | |
| 1-267 | Et | OEt | SO$_2$Et | |
| 1-268 | Et | OiPr | SO$_2$Me | |
| 1-269 | Et | OiPr | SO$_2$Et | |
| 1-270 | Et | O(CH$_2$)$_2$OMe | SO$_2$Me | |
| 1-271 | Et | O(CH$_2$)$_2$OMe | SO$_2$Et | |
| 1-272 | Et | O(CH$_2$)$_3$OMe | SO$_2$Me | |
| 1-273 | Et | O(CH$_2$)$_3$OMe | SO$_2$Et | |
| 1-274 | Et | F | SO$_2$Me | |
| 1-275 | Et | SMe | Cl | |
| 1-276 | Et | SOMe | Cl | |
| 1-277 | Et | SO$_2$Me | Cl | |
| 1-278 | Et | SMe | Br | |
| 1-279 | Et | SOMe | Br | |
| 1-280 | Et | SO$_2$Me | Br | |
| 1-281 | Et | SMe | I | |
| 1-282 | Et | SOMe | I | |
| 1-283 | Et | SO$_2$Me | I | |
| 1-284 | Et | SMe | CF$_3$ | |
| 1-285 | Et | SOMe | CF$_3$ | |
| 1-286 | Et | SO$_2$Me | CF$_3$ | |
| 1-287 | Et | SMe | SO$_2$Me | |
| 1-288 | Et | SOMe | SO$_2$Me | |
| 1-289 | Et | SO$_2$Me | SO$_2$Me | |
| 1-290 | nPr | SMe | Cl | |
| 1-291 | nPr | SOMe | Cl | |
| 1-292 | nPr | SO$_2$Me | Cl | |
| 1-293 | nPr | SMe | CF$_3$ | |
| 1-294 | nPr | SOMe | CF$_3$ | |
| 1-295 | nPr | SO$_2$Me | CF$_3$ | |
| 1-296 | iPr | SMe | Cl | |
| 1-297 | iPr | SOMe | Cl | |
| 1-298 | iPr | SO$_2$Me | Cl | |
| 1-299 | iPr | SMe | CF$_3$ | |
| 1-300 | iPr | SOMe | CF$_3$ | |

TABLE 1-continued

Compounds according to the invention of the formula (I) in which A represents CY, B represents N and R represents 2-methoxyethyl

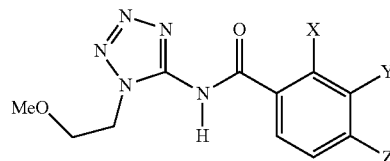

| No. | X | Y | Z | Physical data ($^1$H-NMR, DMSO-$d_6$, 400 MHz) |
|---|---|---|---|---|
| 1-301 | iPr | SO$_2$Me | CF$_3$ | |
| 1-302 | cPr | SMe | CF$_3$ | |
| 1-303 | cPr | SO$_2$Me | CF$_3$ | |
| 1-304 | CF$_3$ | O(CH$_2$)$_2$OMe | F | |
| 1-305 | CF$_3$ | O(CH$_2$)$_3$OMe | F | |
| 1-306 | CF$_3$ | OCH$_2$CONMe$_2$ | F | |
| 1-307 | CF$_3$ | [1,4]dioxan-2-ylmethoxy | F | |
| 1-308 | CF$_3$ | O(CH$_2$)$_2$OMe | Cl | |
| 1-309 | CF$_3$ | O(CH$_2$)$_3$OMe | Cl | |
| 1-310 | CF$_3$ | OCH$_2$CONMe$_2$ | Cl | |
| 1-311 | CF$_3$ | [1,4]dioxan-2-ylmethoxy | Cl | |
| 1-312 | CF$_3$ | O(CH$_2$)$_2$OMe | Br | |
| 1-313 | CF$_3$ | O(CH$_2$)$_2$OMe | Br | |
| 1-314 | CF$_3$ | O(CH$_2$)$_3$OMe | Br | |
| 1-315 | CF$_3$ | OCH$_2$CONMe$_2$ | Br | |
| 1-316 | CF$_3$ | [1,4]dioxan-2-ylmethoxy | Br | |
| 1-317 | CF$_3$ | O(CH$_2$)$_2$OMe | I | |
| 1-318 | CF$_3$ | O(CH$_2$)$_3$OMe | I | |
| 1-319 | CF$_3$ | OCH$_2$CONMe$_2$ | I | |
| 1-320 | CF$_3$ | [1,4]dioxan-2-ylmethoxy | I | |
| 1-321 | CF$_3$ | F | SO$_2$Me | |
| 1-322 | CF$_3$ | F | SO$_2$Et | |
| 1-323 | CF$_3$ | O(CH$_2$)$_2$OMe | SO$_2$Me | |
| 1-324 | CF$_3$ | O(CH$_2$)$_2$OMe | SO$_2$Et | |
| 1-325 | CF$_3$ | O(CH$_2$)$_3$OMe | SO$_2$Me | |
| 1-326 | CF$_3$ | O(CH$_2$)$_3$OMe | SO$_2$Et | |
| 1-327 | CF$_3$ | OCH$_2$CONMe$_2$ | SO$_2$Me | |
| 1-328 | CF$_3$ | OCH$_2$CONMe$_2$ | SO$_2$Et | |
| 1-329 | CF$_3$ | [1,4]dioxan-2-ylmethoxy | SO$_2$Me | |
| 1-330 | CF$_3$ | [1,4]dioxan-2-ylmethoxy | SO$_2$Et | |
| 1-331 | F | SMe | CF$_3$ | |
| 1-332 | F | SOMe | CF$_3$ | |
| 1-333 | F | SO$_2$Me | CF$_3$ | |
| 1-334 | Cl | SMe | H | |
| 1-335 | Cl | SOMe | H | |
| 1-336 | Cl | SO$_2$Me | H | |
| 1-337 | Cl | SEt | H | |
| 1-338 | Cl | SOEt | H | |
| 1-339 | Cl | SO$_2$Et | H | |
| 1-340 | Cl | S(CH$_2$)$_2$OMe | H | |
| 1-341 | Cl | SO(CH$_2$)$_2$OMe | H | |
| 1-342 | Cl | SO$_2$(CH$_2$)$_2$OMe | H | |
| 1-343 | Cl | SMe | Me | 7.40-7.42 (m, 1H), 7.08-7.10 (m, 1H), 4.30-4.60 (m, 2H), 3.70-3.75 (m, 2H), 3.35-3.50 (m, 2H), 2.54 (s, 3H), 2.29 (s, 3H) |
| 1-344 | Cl | SOMe | Me | 9.52 (bs, 1H), 7.62 (d, 1H), 7.30 (d, 1H), 4.60 (t, 2H), 3.82 (t, 2H), 3.37 (s, 3H), 2.98 (s, 3H), 2.78 (s, 3H) |
| 1-345 | Cl | SO$_2$Me | Me | 9.45 (bs, 1H), 7.69 (d, 1H), 7.39 (d, 1H), 4.59 (t, 2H), 3.82 (t, 2H), 3.40 (s, 3H), 3.29 (s, 3H), 2.83 (s, 3H) |
| 1-346 | Cl | SEt | Me | |
| 1-347 | Cl | SOEt | Me | |
| 1-348 | Cl | SO$_2$Et | Me | |
| 1-349 | Cl | Me | Cl | 9.71 (brs, 1H), 7.49 (d, 1H), 7.42 (d, 1H), 4.62 (t, 2H), 3.83 (t, 2H), 3.35 (s, 3H), 2.53 (s, 3H) |
| 1-350 | Cl | CH$_2$-pyrrolidin-2-on-1-yl | Cl | 9.8 (brs, 1H), 7.60 (d, 1H), 7.50 (d, 1H), 4.83 (s, 2H), 4.61 (t, 2H), 3.83 (t, 2H), 3.38 (s, 3H), 3.13 (m, 2H), 2.39 (m, 2H), 1.96 (m, 2H) |

TABLE 1-continued

Compounds according to the invention of the formula (I) in which A represents CY, B represents N and R represents 2-methoxyethyl

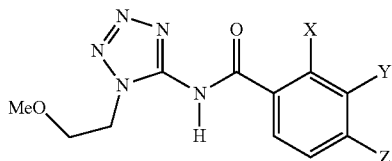

| No. | X | Y | Z | Physical data ($^1$H-NMR, DMSO-$d_6$, 400 MHz) |
|---|---|---|---|---|
| 1-351 | Cl | CH$_2$(4-methyl-3-isopropoxy-1,2,4-triazolin-5-on-1-yl) | Cl | |
| 1-352 | Cl | CH$_2$(4-methyl-3-trifluoroethoxy-1,2,4-triazolin-5-on-1-yl) | Cl | |
| 1-353 | Cl | NH$_2$ | Cl | 9.55 (brs, 1H), 7.32 (d, 1H), 7.01 (d, 1H), 4.71 (s, 2H), 4.61 (t, 2H), 3.82 (t, 2H), 3.35 (s, 3H) |
| 1-354 | Cl | NHAc | Cl | |
| 1-355 | Cl | NHCON(Me)OMe | Cl | |
| 1-356 | Cl | NHCH$_2$CONHEt | Cl | |
| 1-357 | Cl | NHCH$_2$CONHiPr | Cl | |
| 1-358 | Cl | NHCHMeCONHEt | Cl | |
| 1-359 | Cl | imidazolidin-2-on-1-yl | Cl | 11.4 (brs, 1H), 7.49 (d, 1H), 7.42 (d, 1H), 6.02 (brs, 1H), 4.64 (t, 2H), 3.85-3.68 (m, 6H), 3.33 (s, 3H) |
| 1-360 | Cl | 1-methyl-1,2,4-triazolidin-3,5-dion-4-yl | Cl | 10.6 (brs, 1H), 9.8 (brs, 1H), 7.70 (d, 1H), 7.54 (d, 1H), 4.65 (t, 2H), 3.83 (t, 2H), 3.35 (s, 3H), 3.33 (s, 3H) |
| 1-361 | Cl | OMe | Cl | 9.85 (bs, 1H), 7.48 (d, 1H), 7.45 (d, 1H), 4.62 (t, 2H), 3.94 (s, 3H), 3.83 (t, 2H), 3.36 (s, 3H) |
| 1-362 | Cl | OEt | Cl | 9.90 (bs, 1H), 7.46 (d, 1H), 7.44 (d, 1H), 4.63 (t, 2H), 4.13 (q, 2H), 3.83 (t, 2H), 3.36 (s, 3H), 1.48 (t, 3H) |
| 1-363 | Cl | OPr | Cl | |
| 1-364 | Cl | O-allyl | Cl | |
| 1-365 | Cl | OCH$_2$CHF$_2$ | Cl | |
| 1-366 | Cl | O(CH$_2$)$_2$OMe | Cl | 9.32 (bs, 1H), 7.47 (d, 1H), 7.45 (d, 1H), 4.59 (t, 2H), 4.21 (t, 2H), 3.81 (q, 2H), 3.46 (s, 3H), 3.36 (s, 3H) |
| 1-367 | Cl | O(CH$_2$)$_3$OMe | Cl | |
| 1-368 | Cl | OCH$_2$(CO)NMe$_2$ | Cl | 9.95 (brs, 1H), 7.80 (d, 1H), 7.44 (d, 1H), 4.68 (s, 2H), 4.60 (t, 2H), 3.83 (t, 2H), 3.36 (s, 1H) 3.09 (s, 3H), 3.01 (s, 3H) |
| 1-369 | Cl | O(CH$_2$)-5-pyrrolidin-2-one | Cl | |
| 1-370 | Cl | Cl | Cl | 9.95 (brs, 1H), 7.58 (d, 1H), 7.54 (d, 1H), 4.64 (t, 2H), 3.84 (t, 2H), 3.37 (s, 1H) |
| 1-371 | Cl | SMe | Cl | |
| 1-372 | Cl | SOMe | Cl | |
| 1-373 | Cl | SO$_2$Me | Cl | |
| 1-374 | Cl | SEt | Cl | |
| 1-375 | Cl | SOEt | Cl | |
| 1-376 | Cl | SO$_2$Et | Cl | |
| 1-377 | Cl | Me | Br | |
| 1-378 | Cl | CH$_2$(4-methyl-3-isopropoxy-1,2,4-triazolin-5-on-1-yl) | Br | |
| 1-379 | Cl | CH$_2$(4-methyl-3-trifluoroethoxy-1,2,4-triazolin-5-on-1-yl) | Br | |
| 1-380 | Cl | NHAc | Br | |
| 1-381 | Cl | NHCON(Me)OMe | Br | |
| 1-382 | Cl | NHCH$_2$CONHEt | Br | |
| 1-383 | Cl | NHCH$_2$CONHiPr | Br | |
| 1-384 | Cl | NHCHMeCONHEt | Br | |

TABLE 1-continued

Compounds according to the invention of the formula (I) in which A represents CY, B represents N and R represents 2-methoxyethyl

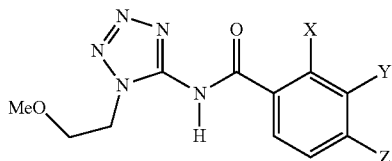

| No. | X | Y | Z | Physical data ($^1$H-NMR, DMSO-$d_6$, 400 MHz) |
|---|---|---|---|---|
| 1-385 | Cl | OMe | Br | 9.49 (bs, 1H), 7.62 (d, 1H), 7.40 (d, 1H), 4.60 (t, 2H), 3.92 (s, 3H), 3.82 (t, 2H), 3.37 (s, 3H), |
| 1-386 | Cl | OEt | Br | |
| 1-387 | Cl | OPr | Br | |
| 1-388 | Cl | OAllyl | Br | |
| 1-389 | Cl | OCH$_2$CHF$_2$ | Br | |
| 1-390 | Cl | O(CH$_2$)$_2$OMe | Br | 11.71 (bs, 1H), 7.81 (d, 1H), 7.40 (d, 1H), 4.56 (t, 2H), 4.24 (t, 2H), 3.77 (t, 2H), 3.74 (t, 2H), 3.35 (s, 3H), 3.23 (s, 3H) |
| 1-391 | Cl | O(CH$_2$)$_3$OMe | Br | |
| 1-392 | Cl | OCH$_2$(CO)NMe$_2$ | Br | |
| 1-393 | Cl | O(CH$_2$)-5-pyrrolidin-2-one | Br | |
| 1-394 | Cl | Cl | Br | |
| 1-395 | Cl | SMe | Br | |
| 1-396 | Cl | SOMe | Br | |
| 1-397 | Cl | SO$_2$Me | Br | |
| 1-398 | Cl | SEt | Br | |
| 1-399 | Cl | SOEt | Br | |
| 1-400 | Cl | SO$_2$Et | Br | |
| 1-401 | Cl | Me | SMe | |
| 1-402 | Cl | Me | SO$_2$Me | |
| 1-403 | Cl | Me | SO$_2$Et | |
| 1-404 | Cl | CO$_2$H | SO$_2$Me | |
| 1-405 | Cl | COOMe | SO$_2$Me | |
| 1-406 | Cl | CONMe$_2$ | SO$_2$Me | |
| 1-407 | Cl | CONMe(OMe) | SO$_2$Me | |
| 1-408 | Cl | CH$_2$N(OMe)Et | SO$_2$Me | |
| 1-409 | Cl | CH$_2$OMe | SO$_2$Me | |
| 1-410 | Cl | CH$_2$OMe | SO$_2$Et | |
| 1-411 | Cl | CH$_2$OEt | SO$_2$Me | |
| 1-412 | Cl | CH$_2$OEt | SO$_2$Et | |
| 1-413 | Cl | CH$_2$OiPr | SO$_2$Me | |
| 1-414 | Cl | CH$_2$Ocpentyl | SO$_2$Me | |
| 1-415 | Cl | CH$_2$OCH$_2$CHF$_2$ | SO$_2$Me | |
| 1-416 | Cl | CH$_2$OCH$_2$CF$_3$ | SMe | 9.74 (bs, 1H), 7.70 (d, 1H), 7.27 (d, 1H), 4.99 (s, 2H), 4.61 (t, 2H), 4.27 (q, 2H), 3.72 (t, 2H), 3.29 (s, 3H), 3.22 (s, 3H) |
| 1-417 | Cl | CH$_2$OCH$_2$CF$_3$ | SO$_2$Me | 7.99 (d, 1H), 7.75 (d, 1H), 5.24 (s, 2H), 4.37 (t, 2H), 3.92 (q, 2H), 3.81 (t, 2H), 3.35 (s, 3H), 2.55 (s, 3H) |
| 1-418 | Cl | CH$_2$OCH$_2$CF$_3$ | SO$_2$Et | |
| 1-419 | Cl | CH$_2$OCH$_2$CF$_2$CHF$_2$ | SO$_2$Me | |
| 1-420 | Cl | CH$_2$O(CH$_2$)$_2$OMe | SO$_2$Me | |
| 1-421 | Cl | CH$_2$PO$_3$Me$_2$ | SO$_2$Me | |
| 1-422 | Cl | CH$_2$O-tetrahydrofuran-3-yl | SO$_2$Me | |
| 1-423 | Cl | CH$_2$O-tetrahydrofuran-3-yl | SO$_2$Et | |
| 1-424 | Cl | CH$_2$OCH$_2$-tetrahydrofuran-2-yl | SO$_2$Me | 9.65 (bs, 1H), 8.18 (d, 1H), 7.77 (d, 1H), 5.20 (s, 2H), 4.61 (t, 2H), 4.08 (m, 1H), 3.83 (t, 2H), 3.82-3.58 (m, 4H), 3.37 (s, 3H), 3.33 (s, 3H), 2.0-1.8 (m, 3H), 1.63-1.5 (m, 1H), |
| 1-425 | Cl | CH$_2$OCH$_2$-tetrahydrofuran-2-yl | SO$_2$Et | |
| 1-426 | Cl | CH$_2$OCH$_2$-tetrahydrofuran-3-yl | SO$_2$Me | |
| 1-427 | Cl | CH$_2$OCH$_2$-tetrahydrofuran-3-yl | SO$_2$Et | |
| 1-428 | Cl | 4,5-dihydro-1,2-oxazol-3-yl | SMe | |

TABLE 1-continued

Compounds according to the invention of the formula (I) in which A represents CY, B represents N and R represents 2-methoxyethyl

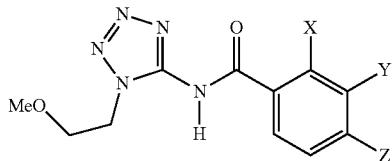

| No. | X | Y | Z | Physical data ($^1$H-NMR, DMSO-$d_6$, 400 MHz) |
|---|---|---|---|---|
| 1-429 | Cl | 4,5-dihydro-1,2-oxazol-3-yl | SO$_2$Me | |
| 1-430 | Cl | 4,5-dihydro-1,2-oxazol-3-yl | SO$_2$Et | |
| 1-431 | Cl | 5-cyanomethyl-4,5-dihydro-1,2-oxazol-3-yl | SO$_2$Me | |
| 1-432 | Cl | 5-cyanomethyl-4,5-dihydro-1,2-oxazol-3 yl | SO$_2$Et | 10.35 (bs, 1H), 8.14 (d, 1H), 7.93 (d, 1H), 5.16 (m, 1H), 4.65 (t, 2H), 3.84 (t, 2H), 3.73 (dd, 1H), 3.38 (s, 3H), 3.37 (q, 2H), 3.27 (dd, 1H), 2.95 (dd, 1H), 2.85 (dd, 1H), 1.31 (t, 3H) |
| 1-433 | Cl | 5-(MeOCH$_2$)-4,5-dihydro-1,2-oxazol-3-yl | SO$_2$Me | |
| 1-434 | Cl | 5-(MeOCH$_2$)-4,5-dihydro-1,2-oxazol-3-yl | SO$_2$Et | |
| 1-435 | Cl | 5-Me-5-(MeOCH$_2$)-4,5-dihydro-1,2-oxazol-3-yl | SO$_2$Me | |
| 1-436 | Cl | 5-Me-5-(MeOCH$_2$)-4,5-dihydro-1,2-oxazol-3-yl | SO$_2$Et | |
| 1-437 | Cl | NH$_2$ | SO$_2$Me | |
| 1-438 | Cl | NHMe | SO$_2$Me | |
| 1-439 | Cl | NMe$_2$ | SO$_2$Me | |
| 1-440 | Cl | NH(CH$_2$)$_2$OMe | SO$_2$Me | |
| 1-441 | Cl | NH(CH$_2$)$_2$OMe | SO$_2$Et | |
| 1-442 | Cl | NH(CH$_2$)$_2$OEt | SO$_2$Me | |
| 1-443 | Cl | NH(CH$_2$)$_3$OMe | SO$_2$Me | |
| 1-444 | Cl | NH(CH$_2$)$_3$OMe | SO$_2$Et | |
| 1-445 | Cl | NH(CH$_2$)$_4$OMe | SO$_2$Me | |
| 1-446 | Cl | NH(CH$_2$)$_4$OMe | SO$_2$Et | |
| 1-447 | Cl | pyrazol-1-yl | SO$_2$Me | |
| 1-448 | Cl | OMe | SO$_2$Me | |
| 1-449 | Cl | OMe | SO$_2$Et | |
| 1-450 | Cl | OEt | SO$_2$Me | 9.41 (bs, 1H), 8.02 (d, 1H), 7.56 (bd, 1H), 4.61 (t, 2H), 4.32 (q, 2H), 3.84 (t, 2H), 3.39 (s, 3H), 3.29 (s, 3H), 1.42 (t, 3H) |
| 1-451 | Cl | OEt | SO$_2$Et | |
| 1-452 | Cl | OPr | SO$_2$Me | 9.56 (bs, 1H), 8.02 (d, 1H), 7.55 (bd, 1H), 4.62 (t, 2H), 4.22 (t, 2H), 3.84 (t, 2H), 3.39 (s, 3H), 3.28 (s, 3H), 1.95 (quin, 2H), 1.09 (t, 3H) |
| 1-453 | Cl | OPr | SO$_2$Et | 11.86 (bs, 1H), 7.93 (d, 1H), 7.71 (d, 1H), 4.58 (t, 2H), 4.15 (t, 2H), 3.78 (t, 2H), 3.51 (q, 2H), 3.24 (s, 3H), 1.88 (sex, 2H), 1.13 (t, 3H), 1.05 (t, 3H) |
| 1-454 | Cl | OiPr | SO$_2$Me | |
| 1-455 | Cl | OiPr | SO$_2$Et | |
| 1-456 | Cl | OAllyl | SO$_2$Me | 9.35 (bs, 1H), 8.03 (d, 1H), 7.58 (bd, 1H), 6.19 (m, 1H), 5.51 (dd, 1H), 5.37 (dd, 1H), 4.75 (d, 2H), 4.61 (t, 2H), 3.84 (t, 2H), 3.40 (s, 3H), 3.28 (s, 3H) |
| 1-457 | Cl | Oallyl | SO$_2$Et | |
| 1-458 | Cl | Opropargyl | SO$_2$Me | 9.63 (bs, 1H), 8.03 (d, 1H), 7.61 (bd, 1H), 4.92 (s, 2H), 4.63 (t, 2H), 3.84 (t, 2H), 3.40 (s, 3H), 3.32 (s, 3H), 2.66 (t, 1H) |
| 1-459 | Cl | Opropargyl | SO$_2$Et | |

TABLE 1-continued

Compounds according to the invention of the formula (I) in which A represents CY, B represents N and R represents 2-methoxyethyl

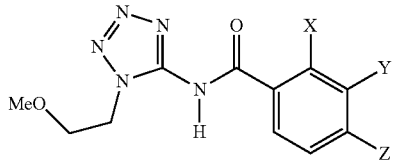

| No. | X | Y | Z | Physical data ($^1$H-NMR, DMSO-$d_6$, 400 MHz) |
|---|---|---|---|---|
| 1-460 | Cl | O(CH$_2$)$_2$F | SO$_2$Me | 9.50 (bs, 1H), 8.04 (d, 1H), 7.52 (bd, 1H), 3.89-3.91 (m, 1H), 4.77-4.79 (m, 1H), 4.62 (t, 2H), 4.55 (bs, 1H), 4.48 (bs, 1H), 3.84 (t, 2H), 3.40 (s, 3H), 3.31 (s, 3H) |
| 1-461 | Cl | O(CH$_2$)$_2$F | SO$_2$Et | |
| 1-462 | Cl | O(CH$_2$)$_2$Cl | SO$_2$Me | 9.56 (bs, 1H), 8.04 (d, 1H), 7.52 (bd, 1H), 4.62 (t, 2H), 4.51 (t, 2H), 3.95 (t, 2H), 3.84 (t, 2H), 3.41 (s, 3H), 3.32 (s, 3H) |
| 1-463 | Cl | O(CH$_2$)$_2$Cl | SO$_2$Et | 9.61 (bs, 1H), 8.02 (d, 1H), 7.60 (bd, 1H), 4.62 (t, 2H), 4.50 (t, 2H), 3.94 (t, 2H), 3.84 (t, 2H), 3.48 (q, 2H), 3.40 (s, 3H), 1.28 (t, 3H) |
| 1-464 | Cl | OCH$_2$cPr | SO$_2$Me | 9.42 (bs, 1H), 8.02 (d, 1H), 7.55 (d, 1H), 4.61 (t, 2H), 4.09 (d, 2H), 3.83 (t, 2H), 3.39 (s, 3H), 3.33 (s, 3H), 1.40-1.49 (m, 1H), 0.65-0.70 (m, 2H), 0.45-0.50 (m, 2H) |
| 1-465 | Cl | OCH$_2$cPr | SO$_2$Et | 9.50 (bs, 1H), 8.00 (d, 1H), 7.56 (d, 1H), 4.62 (t, 2H), 4.08 (d, 2H), 3.84 (t, 2H), 3.51 (q, 2H), 3.38 (s, 3H), 1.42-1.46 (m, 1H), 1.27 (t, 3H), 0.65-0.70 (m, 2H), 0.44-0.48 (m, 2H) |
| 1-466 | Cl | OCH$_2$cBu | SO$_2$Me | 9.41 (bs, 1H), 8.02 (d, 1H), 7.55 (d, 1H), 4.62 (t, 2H), 4.24 (d, 2H), 3.84 (t, 2H), 3.39 (s, 3H), 3.27 (s, 3H), 2.89-2.98 (m, 1H), 2.13-2.21 (m, 2H), 1.90-2.05 (m, 4H) |
| 1-467 | Cl | OCH$_2$cBu | SO$_2$Et | |
| 1-468 | Cl | O(CH$_2$)$_2$OMe | SO$_2$Me | 7.76 (d, 1H), 7.47 (d, 1H), 4.33 (t, 2H), 4.27 (t, 2H), 3.77 (q, 2H), 3.71 (t, 2H), 3.36 (s, 6H), 3.29 (s, 3H) |
| 1-469 | Cl | O(CH$_2$)$_2$OMe | SO$_2$Et | |
| 1-470 | Cl | O(CH$_2$)$_2$OEt | SO$_2$Me | |
| 1-471 | Cl | O(CH$_2$)$_3$OMe | SO$_2$Me | |
| 1-472 | Cl | O(CH$_2$)$_3$OMe | SO$_2$Et | |
| 1-473 | Cl | O(CH$_2$)$_4$OMe | SO$_2$Me | |
| 1-474 | Cl | O(CH$_2$)$_4$OMe | SO$_2$Et | |
| 1-475 | Cl | O(CH$_2$)$_2$OCF$_3$ | SO$_2$Me | 11.88 (bs, 1H), 7.97 (d, 1H), 7.75 (d, 1H), 4.57 (q, 2H), 4.54-4.56 (m, 2H), 4.43-4.48 (m, 2H), 3.78 (t, 2H), 3.40 (s, 3H), 3.24 (s, 3H) |
| 1-476 | Cl | O(CH$_2$)$_2$OCF$_3$ | SO$_2$Et | 11.88 (bs, 1H), 7.96 (d, 1H), 7.76 (d, 1H), 4.58 (t, 2H), 4.53-4.56 (m, 2H), 4.43-4.46 (m, 2H), 3.78 (t, 2H), 3.42 (q, 2H), 3.24 (s, 3H), 1.15 (t, 3H) |
| 1-477 | Cl | O(CH$_2$)$_2$SMe | SO$_2$Me | |
| 1-478 | Cl | O(CH$_2$)$_2$SEt | SO$_2$Me | |
| 1-479 | Cl | O(CH$_2$)$_3$SMe | SO$_2$Me | |
| 1-480 | Cl | OCH$_2$-tetrahydrofuran-2-yl | SO$_2$Me | |
| 1-481 | Cl | OCH$_2$-tetrahydrofuran-2-yl | SO$_2$Et | |
| 1-482 | Cl | [1,4]dioxan-2-ylmethoxy | SO$_2$Me | |
| 1-483 | Cl | [1,4]dioxan-2-ylmethoxy | SO$_2$Et | |
| 1-484 | Cl | OCH$_2$(CO)NMe$_2$ | SO$_2$Me | 10.6 (brs, 1H), 8.02 (d, 1H), 7.63 (d, 1H), 4.94 (s, 2H), 4.64 (t, 2H), 3.84 (t, 2H), 3.44 (s, 3H), 3.37 (s, 3H), 3.03 (s, 3H), 2.93 (s, 3H) |

TABLE 1-continued

Compounds according to the invention of the formula (I) in which A represents CY, B represents N and R represents 2-methoxyethyl

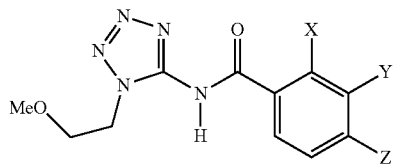

| No. | X | Y | Z | Physical data ($^1$H-NMR, DMSO-$d_6$, 400 MHz) |
|---|---|---|---|---|
| 1-485 | Cl | OCH$_2$(CO)NMe$_2$ | SO$_2$Et | 10.7 (bs, 1H), 8.00 (d, 1H), 7.63 (d, 1H), 4.93 (s, 2H), 4.65 (t, 2H), 3.83 (t, 2H), 3.64 (q, 2H), 3.36 (s, 3H), 3.02 (s, 3H), 2.94 (s, 3H), 1.26 (t, 3H) |
| 1-486 | Cl | F | SMe | |
| 1-487 | Cl | Cl | SO$_2$Me | 9.9 (brs, 1H), 8.21 (d, 1H), 7.74 (d, 1H), 4.63 (t, 2H), 3.84 (t, 2H), 3.39 (s, 3H), 3.33 (s, 3H) |
| 1-488 | Cl | SMe | SO$_2$Me | 11.9 (brs, 1H), 8.15 (d, 1H), 7.94 (d, 1H), 4.58 (t, 2H), 3.78 (t, 2H), 3.59 (s, 3H), 3.24 (s, 3H), 2.50 (s, 3H) |
| 1-489 | Cl | SOMe | SO$_2$Me | 11.8 (brs, 1H), 8.05 (d, 1H), 7.89 (d, 1H), 4.42 (t, 2H), 3.73 (t, 2H), 3.51 (s, 3H), 3.22 (s, 3H), 3.18 (s, 3H), |
| 1-490 | Cl | SO$_2$Me | SO$_2$Me | 12.0 (brs, 1H), 8.39 (d, 1H), 8.27 (d, 1H), 4.59 (t, 2H), 3.78 (t, 2H), 3.67 (s, 3H), 3.58 (s, 3H), 3.24 (s, 3H), |
| 1-491 | Br | OMe | Br | 9.80 (brs, 1H), 7.65 (d, 1H), 7.30 (d, 1H), 4.65 (t, 2H), 3.92 (s, 3H), 3.84 (t, 2H), 3.36 (s, 3H) |
| 1-492 | Br | O(CH$_2$)$_2$OMe | Br | |
| 1-493 | Br | O(CH$_2$)$_3$OMe | Br | |
| 1-494 | Br | OMe | SO$_2$Me | 9.60 (brs, 1H), 7.89 (d, 1H), 7.23 (d, 1H), 4.66 (t, 2H), 4.06 (s, 3H), 3.82 (t, 2H), 3.41 (s, 3H), 3.22 (s, 3H) |
| 1-495 | Br | OMe | SO$_2$Et | |
| 1-496 | Br | OEt | SO$_2$Me | |
| 1-497 | Br | OEt | SO$_2$Et | |
| 1-498 | Br | OPr | SO$_2$Me | |
| 1-499 | Br | OPr | SO$_2$Et | |
| 1-500 | Br | O(CH$_2$)$_2$OMe | SO$_2$Me | |
| 1-501 | Br | O(CH$_2$)$_2$OMe | SO$_2$Et | |
| 1-502 | Br | O(CH$_2$)$_3$OMe | SO$_2$Me | |
| 1-503 | Br | O(CH$_2$)$_3$OMe | SO$_2$Et | |
| 1-504 | Br | O(CH$_2$)$_4$OMe | SO$_2$Me | |
| 1-505 | Br | O(CH$_2$)$_4$OMe | SO$_2$Et | |
| 1-506 | Br | [1,4]dioxan-2-ylmethoxy | SO$_2$Me | |
| 1-507 | Br | [1,4]dioxan-2-ylmethoxy | SO$_2$Et | |
| 1-508 | I | O(CH$_2$)$_2$OMe | SO$_2$Me | |
| 1-509 | I | O(CH$_2$)$_2$OMe | SO$_2$Et | |
| 1-510 | I | O(CH$_2$)$_3$OMe | SO$_2$Me | |
| 1-511 | I | O(CH$_2$)$_3$OMe | SO$_2$Et | |
| 1-512 | I | O(CH$_2$)$_4$OMe | SO$_2$Me | |
| 1-513 | I | O(CH$_2$)$_4$OMe | SO$_2$Et | |
| 1-514 | I | [1,4]dioxan-2-ylmethoxy | SO$_2$Me | |
| 1-515 | I | [1,4]dioxan-2-ylmethoxy | SO$_2$Et | |
| 1-516 | OH | SO$_2$Me | CF$_3$ | |
| 1-517 | OMe | SMe | CF$_3$ | 7.76 (d, H), 7.68 (d, 1H), 4.53 (t, 2H), 3.96 (s, 3H), 3.77 (t, 2H), 3.24 (s, 3H), 2.44 (s, 3H) |
| 1-518 | OMe | SOMe | CF$_3$ | 7.76 (d, 1H), 7.68 (d, 1H), 4.53 (t, 2H), 3.96 (s, 3H), 3.77 (t, 2H), 3.24 (s, 3H), 2.44 (s, 3H) |
| 1-519 | OMe | SO$_2$Me | CF$_3$ | |
| 1-520 | OMe | SEt | CF$_3$ | |
| 1-521 | OMe | SOEt | CF$_3$ | |
| 1-522 | OMe | SO$_2$Et | CF$_3$ | |
| 1-523 | OMe | S(CH$_2$)$_2$OMe | CF$_3$ | |
| 1-524 | OMe | SO(CH$_2$)$_2$OMe | CF$_3$ | |
| 1-525 | OMe | SO$_2$(CH$_2$)$_2$OMe | CF$_3$ | |

TABLE 1-continued

Compounds according to the invention of the formula (I) in which A represents CY, B represents N and R represents 2-methoxyethyl

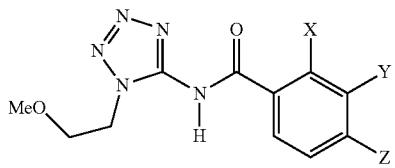

| No. | X | Y | Z | Physical data ($^1$H-NMR, DMSO-$d_6$, 400 MHz) |
|---|---|---|---|---|
| 1-526 | OMe | CH$_2$N(SO$_2$Me)Et | Cl | |
| 1-527 | OMe | NHCOMe | Cl | 10.26 (bs, 1H), 7.99 (d, 1H), 7.38 (d, 1H), 4.57 (t, 2H), 3.95 (s, 3H), 3.80 (t, 2H), 3.30 (s, 3H), 2.30 (bs, 3H) |
| 1-528 | OMe | NHCOEt | Cl | |
| 1-529 | OMe | NHCOiPr | Cl | |
| 1-530 | OMe | NHCOcycPr | Cl | |
| 1-531 | OMe | NHCOCHCMe$_2$ | Cl | |
| 1-532 | OMe | NHCOPh | Cl | |
| 1-533 | OMe | SMe | Cl | |
| 1-534 | OMe | SOMe | Cl | |
| 1-535 | OMe | SO$_2$Me | Cl | |
| 1-536 | OMe | SEt | Cl | |
| 1-537 | OMe | SOEt | Cl | |
| 1-538 | OMe | SO$_2$Et | Cl | |
| 1-539 | OMe | S(CH$_2$)$_2$OMe | Cl | |
| 1-540 | OMe | SO(CH$_2$)$_2$OMe | Cl | |
| 1-541 | OMe | SO$_2$(CH$_2$)$_2$OMe | Cl | |
| 1-542 | OEt | SMe | Cl | |
| 1-543 | OEt | SOMe | Cl | |
| 1-544 | OEt | SO$_2$Me | Cl | |
| 1-545 | OCH$_2$c-Pr | SMe | CF$_3$ | |
| 1-546 | OCH$_2$c-Pr | SOMe | CF$_3$ | |
| 1-547 | OCH$_2$c-Pr | SO$_2$Me | CF$_3$ | |
| 1-548 | OCH$_2$c-Pr | SEt | CF$_3$ | |
| 1-549 | OCH$_2$c-Pr | SOEt | CF$_3$ | |
| 1-550 | OCH$_2$c-Pr | SO$_2$Et | CF$_3$ | |
| 1-551 | OCH$_2$c-Pr | S(CH$_2$)$_2$OMe | CF$_3$ | |
| 1-552 | OCH$_2$c-Pr | SO(CH$_2$)$_2$OMe | CF$_3$ | |
| 1-553 | OCH$_2$c-Pr | SO$_2$(CH$_2$)$_2$OMe | CF$_3$ | |
| 1-554 | OCH$_2$c-Pr | SMe | Cl | |
| 1-555 | OCH$_2$c-Pr | SOMe | Cl | |
| 1-556 | OCH$_2$c-Pr | SO$_2$Me | Cl | |
| 1-557 | OCH$_2$c-Pr | SEt | Cl | |
| 1-558 | OCH$_2$c-Pr | SOEt | Cl | |
| 1-559 | OCH$_2$c-Pr | SO$_2$Et | Cl | |
| 1-560 | OCH$_2$c-Pr | S(CH$_2$)$_2$OMe | Cl | |
| 1-561 | OCH$_2$c-Pr | SO(CH$_2$)$_2$OMe | Cl | |
| 1-562 | OCH$_2$c-Pr | SO$_2$(CH$_2$)$_2$OMe | Cl | |
| 1-563 | OCH$_2$c-Pr | SMe | SO$_2$Me | |
| 1-564 | OCH$_2$c-Pr | SOMe | SO$_2$Me | |
| 1-565 | OCH$_2$c-Pr | SO$_2$Me | SO$_2$Me | |
| 1-566 | OCH$_2$c-Pr | SEt | SO$_2$Me | |
| 1-567 | OCH$_2$c-Pr | SOEt | SO$_2$Me | |
| 1-568 | OCH$_2$c-Pr | SO$_2$Et | SO$_2$Me | |
| 1-569 | OCH$_2$c-Pr | S(CH$_2$)$_2$OMe | SO$_2$Me | |
| 1-570 | OCH$_2$c-Pr | SO(CH$_2$)$_2$OMe | SO$_2$Me | |
| 1-571 | OCH$_2$c-Pr | SO$_2$(CH$_2$)$_2$OMe | SO$_2$Me | |
| 1-572 | OSO$_2$Me | SMe | CF$_3$ | 11.87 (brs, 1H), 7.98 (d, H), 7.94 (d, 1H), 4.57 (t, 2H), 3.78 (t, 2H), 3.61 (s, 3H), 3.24 (s, 3H), 2.52 (s, 3H) |
| 1-573 | OSO$_2$Me | SOMe | CF$_3$ | |
| 1-574 | OSO$_2$Me | SO$_2$Me | CF$_3$ | |
| 1-575 | SMe | SMe | H | |
| 1-576 | SO$_2$Me | SO$_2$Me | H | |
| 1-577 | SMe | SMe | F | |
| 1-578 | SMe | SEt | F | |
| 1-579 | SO$_2$Me | NHEt | Cl | |
| 1-580 | SMe | OCH$_2$CHF$_2$ | Br | |
| 1-581 | SO$_2$Me | F | CF$_3$ | |
| 1-582 | SO$_2$Me | NH$_2$ | CF$_3$ | |

TABLE 1-continued

Compounds according to the invention of the formula (I) in which A represents CY, B represents N and R represents 2-methoxyethyl

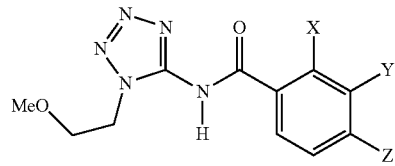

| No. | X | Y | Z | Physical data ($^1$H-NMR, DMSO-$d_6$, 400 MHz) |
|---|---|---|---|---|
| 1-583 | Cl | SMe | CF$_3$ | 11.9 (brs, 1H), 7.98 (d, 1H), 7.93 (d, 1H), 4.59 (t, 2H), 3.78 (t, 2H), 3.24 (s, 3H), 2.45 (s, 3H) |
| 1-584 | Cl | SOMe | CF$_3$ | 11.9 (brs, 1H), 8.07 (s, 2H), 4.59 (t, 2H), 3.78 (t, 2H), 3.24 (s, 3H), 3.16 (s, 3H) |
| 1-585 | Cl | SO$_2$Me | CF$_3$ | 12.0 (brs, 1H), 8.21 (2d, 2H), 4.59 (t, 2H), 3.78 (t, 2H), 3.54 (s, 3H), 3.24 (s, 3H) |
| 1-586 | Cl | OCHF$_2$ | SO$_2$Me | 10.95 (bs, 1H), 8.11 (d, 1H) 7.74 (bd, 1H), 6.84 (t, 1H), 4.64 (t, 2H), 3.84 (t, 2H), 3.40 (s, 3H), 3.28 (s, 3H) |
| 1-587 | Cl | OCHF$_2$ | SO$_2$Et | 10.05 (bs, 1H), 8.09 (d, 1H), 7.75 (bd, 1H), 6.86 (t, 1H), 4.64 (t, 2H), 3.84 (t, 2H), 3.40 (q, 2H), 3.40 (s, 3H), 1.30 (t, 3H) |
| 1-588 | Me | O(CH$_2$)$_2$SOEt | Br | 9.41 (bs, 1H), 7.53 (d, 1H), 7.23 (d, 1H), 4.60 (t, 2H), 4.31-4.42 (m, 2H), 3.83 (t, 2H), 3.37 (s, 3H), 3.23-3.30 (m, 1H), 3.02-3.09 (m, 1H), 2.83-2.94 (m, 2H), 2.54 (s, 3H), 1.42 (t, 3H) |
| 1-589 | Me | O(CH$_2$)$_2$SO$_2$Et | Br | 9.58 (bs, 1H), 7.55 (d, 1H), 7.24 (d, 1H), 4.62 (t, 2H), 4.35 (t, 2H), 3.83 (t, 2H), 3.50 (t, 2H), 3.37 (s, 3H), 3.29 (q, 2H), 2.53 (s, 3H), 1.48 (t, 3H) |
| 1-590 | Cl | O(CH$_2$)$_2$SMe | Cl | 9.71 (bs, 1H), 7.47 (s, 2H), 4.61 (t, 2H), 4.21 (t, 2H), 3.82 (t, 2H), 3.36 (s, 3H), 2.98 (t, 2H), 2.22 (s, 3H) |
| 1-591 | Et | SEt | CF$_3$ | 7.70 (d, 1H), 7.57 (d, 1H), 4.63 (t, 2H), 3.83 (t, 2H), 3.34 (s, 3H), 3.27 (q, 2H), 2.80 (q, 2H), 1.29-1.23 (m, 6H) |
| 1-592 | Et | SOEt | CF$_3$ | 7.74-7.62 (m, 2H), 4.62 (t, 2H), 3.83 (t, 2H), 3.63 (m, 1H), 3.52-3.25 (m, 2H), 3.35 (s, 3H), 2.95 (m, 1H), 1.46 (t, 3H), 1.29 (t, 3H) |
| 1-593 | Et | SO$_2$Et | CF$_3$ | 7.91 (d, 1H), 7.76 (m, 1H), 4.61 (t, 2H), 3.83 (t, 2H), 3.50-3.13 (m, 7H), 1.50 (t, 3H), 1.34 (t, 3H) |
| 1-594 | cPr | SOMe | CF$_3$ | |
| 1-595 | Et | SEt | Cl | |
| 1-596 | Et | SOEt | Cl | |
| 1-597 | Et | SO$_2$Et | Cl | |
| 1-598 | OMe | SMe | CHF$_2$ | 8.21 (d, 1H), 7.64 (d, 1H), 7.23 (t, 1H), 4.60 (t, 2H), 4.12 (s, 3H), 3.82 (t, 2H), 3.35 (s, 3H), 2.46 (s, 3H) in CDCl$_3$ |
| 1-599 | OMe | SOMe | CHF$_2$ | |
| 1-600 | OMe | SO$_2$Me | CHF$_2$ | |
| 1-601 | OMe | SEt | CHF$_2$ | |
| 1-602 | OMe | SOEt | CHF$_2$ | |
| 1-603 | OMe | SO$_2$Et | CHF$_2$ | |
| 1-604 | OMe | S(CH$_2$)$_2$OMe | CHF$_2$ | |
| 1-605 | OMe | SO(CH$_2$)$_2$OMe | CHF$_2$ | |
| 1-606 | OMe | SO$_2$(CH$_2$)$_2$OMe | CHF$_2$ | |
| 1-607 | CH$_2$OMe | SMe | Cl | |
| 1-608 | CH$_2$OMe | SOMe | Cl | |
| 1-609 | CH$_2$OMe | SO$_2$Me | Cl | |
| 1-610 | CH$_2$OMe | SEt | Cl | |
| 1-611 | CH$_2$OMe | SOEt | Cl | |
| 1-612 | CH$_2$OMe | SO$_2$Et | Cl | |

TABLE 1-continued

Compounds according to the invention of the formula (I) in which A represents CY, B represents N and R represents 2-methoxyethyl

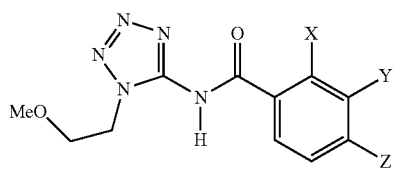

| No. | X | Y | Z | Physical data ($^1$H-NMR, DMSO-$d_6$, 400 MHz) |
|---|---|---|---|---|
| 1-613 | CH$_2$OMe | S(CH$_2$)$_2$OMe | Cl | |
| 1-614 | CH$_2$OMe | SO(CH$_2$)$_2$OMe | Cl | |
| 1-615 | CH$_2$OMe | SO$_2$(CH$_2$)$_2$OMe | Cl | |
| 1-616 | CH$_2$OMe | SMe | CF$_3$ | |
| 1-617 | CH$_2$OMe | SOMe | CF$_3$ | |
| 1-618 | CH$_2$OMe | SO$_2$Me | CF$_3$ | |
| 1-619 | CH$_2$OMe | SEt | CF$_3$ | |
| 1-620 | CH$_2$OMe | SOEt | CF$_3$ | |
| 1-621 | CH$_2$OMe | SO$_2$Et | CF$_3$ | |
| 1-622 | CH$_2$OMe | S(CH$_2$)$_2$OMe | CF$_3$ | |
| 1-623 | CH$_2$OMe | SO(CH$_2$)$_2$OMe | CF$_3$ | |
| 1-624 | CH$_2$OMe | SO$_2$(CH$_2$)$_2$OMe | CF$_3$ | |
| 1-625 | CH$_2$OMe | SMe | SO$_2$Me | |
| 1-626 | CH$_2$OMe | SOMe | SO$_2$Me | |
| 1-627 | CH$_2$OMe | SO$_2$Me | SO$_2$Me | |
| 1-628 | CH$_2$OMe | SEt | SO$_2$Me | |
| 1-629 | CH$_2$OMe | SOEt | SO$_2$Me | |
| 1-630 | CH$_2$OMe | SO$_2$Et | SO$_2$Me | |
| 1-631 | CH$_2$OMe | S(CH$_2$)$_2$OMe | SO$_2$Me | |
| 1-632 | CH$_2$OMe | SO(CH$_2$)$_2$OMe | SO$_2$Me | |
| 1-633 | CH$_2$OMe | SO$_2$(CH$_2$)$_2$OMe | SO$_2$Me | |
| 1-634 | Et | SEt | SO$_2$Me | |
| 1-635 | Et | SOEt | SO$_2$Me | |
| 1-636 | Et | SO$_2$Et | SO$_2$Me | |
| 1-637 | Cl | S(CH$_2$)$_2$OMe | Cl | |
| 1-638 | Cl | SO(CH$_2$)$_2$OMe | Cl | |
| 1-639 | Cl | SO$_2$(CH$_2$)$_2$OMe | Cl | |
| 1-640 | Cl | SEt | SO$_2$Me | |
| 1-641 | Cl | SOEt | SO$_2$Me | |
| 1-642 | Cl | SO$_2$Et | SO$_2$Me | |
| 1-643 | Cl | S(CH$_2$)$_2$OMe | SO$_2$Me | |
| 1-644 | Cl | SO(CH$_2$)$_2$OMe | SO$_2$Me | |
| 1-645 | Cl | SO$_2$(CH$_2$)$_2$OMe | SO$_2$Me | |
| 1-646 | Cl | SEt | CF$_3$ | |
| 1-647 | Cl | SOEt | CF$_3$ | |
| 1-648 | Cl | SO$_2$Et | CF$_3$ | |
| 1-649 | Cl | S(CH$_2$)$_2$OMe | CF$_3$ | |
| 1-650 | Cl | SO(CH$_2$)$_2$OMe | CF$_3$ | |
| 1-651 | Cl | SO$_2$(CH$_2$)$_2$OMe | CF$_3$ | |

TABLE 2

Compounds according to the invention of the formula (I) in which A represents CY

| No. | B | R | X | Y | Z | Physical data ($^1$H-NMR, DMSO-$d_6$, 400 MHz) |
|---|---|---|---|---|---|---|
| 2-1 | N | (CH$_2$)$_2$OH | Me | SO$_2$Me | CF$_3$ | 7.81 (d, H), 7.72 (d, 1H), 4.35 (brs, 1H), 4.15 (t, 2H), 3.72 (t, 2H), 3.35 (s, 3H), 2.74 (s, 3H) |
| 2-2 | N | (CH$_2$)$_2$OEt | Me | SO$_2$Me | CF$_3$ | 11.8 (brs, 1H), 8.07 (d, H), 8.03 (d, 1H), 4.58 (t, 2H), 3.79 (t, 2H), 3.49 (s, 3H), 3.41 |

TABLE 2-continued

Compounds according to the invention of the formula (I) in which A represents CY

| No. | B | R | X | Y | Z | Physical data (¹H-NMR, DMSO-d₆, 400 MHz) |
|---|---|---|---|---|---|---|
| | | | | | | (q, 2H), 2.76 (s, 3H), 1.02 (t, 3H) |
| 2-3 | CH | (CH₂)₂OMe | Me | SO₂Me | CF₃ | |
| 2-4 | N | (CH₂)₂OBn | Me | SO₂Me | CF₃ | 7.90 (d, 1H), 7.82 (d, 1H), 7.34-7.21 (m, 5H), 4.52 (t, 2H), 4.47 (s, 2H), 3.83 (t, 2H), 3.39 (s, 3H), 2.72 (s, 3H) |
| 2-5 | N | CH₂CMe₂OMe | Me | SO₂Me | CF₃ | 11.6 (brs, 1H), 7.96 (d, H), 7.84 (d, 1H), 4.34 (s, 2H), 3.40 (s, 3H), 3.13 (s, 3H), 2.75 (s, 3H), 1.13 (s, 6H) |
| 2-6 | N | (CH₂)₃OMe | Me | SO₂Me | CF₃ | 7.97 (d, 1H), 7.92 (d, 1H), 4.30 (m, 2H), 3.39 (s, 3H), 3.29 (m, 2H), 3.21 (s, 3H), 2.76 (s, 3H), 2.05 (m, 2H) |
| 2-7 | N | CH₂CN | Me | SO₂Me | CF₃ | 8.15 (d, 1H), 8.11 (d, 1H), 5.79 (s, 2H), 3.45 (s, 3H), 2.75 (s, 3H) |
| 2-8 | N | (CH₂)₂NMe₂ | Me | SO₂Me | CF₃ | 7.88 (d, 1H), 7.82 (d, 1H), 4.27 (m, 2H), 3.71 (m, 2H), 3.36 (s, 3H), 2.75 (m, 2H), 2.15 (s, 6H) |
| 2-9 | N | CH₂SiMe₃ | Me | SO₂Me | CF₃ | 7.95-7.89 (m, 2H), 3.73 (s, 2H), 3.39 (s, 3H), 2.76 (s, 3H), 0.13 (s, 9H) |
| 2-10 | N | (CH₂)₂SiMe₃ | | | | |
| 2-11 | N | CH₂PO(OEt)₃ | | | | |
| 2-12 | N | CH₂SMe | | | | |
| 2-13 | N | (CH₂)₂SMe | Me | SO₂Me | CF₃ | 11.9 (brs, 1H), 8.06 (s, 2H), 4.58 (t, 2H), 3.44 (s, 3H), 3.02 (t, 2H), 2.76 (s, 3H), 2.07 (s, 3H) |
| 2-14 | N | (CH₂)₂SOMe | Me | SO₂Me | CF₃ | 8.13 (d, 1H), 8.06 (d, 1H), 4.85-4.78 (m, 2H), 3.48-3.38 (m, 2H), 3.44 (s, 3H), 2.77 (s, 3H), 2.63 (s, 3H) |
| 2-15 | N | (CH₂)₂SO₂Me | Me | SO₂Me | CF₃ | 7.98 (brs, 2H), 4.73 (t, 2H), 3.81 (t, 2H), 3.40 (s, 3H), 3.05 (s, 3H), 2.76 (s, 3H) |
| 2-16 | N | (CH₂)₂CN | Me | SO₂Me | CF₃ | |
| 2-17 | N | (CH₂)₂NO₂ | Me | SO₂Me | CF₃ | |
| 2-18 | N | CH₂(2-oxopyrrolidin-1-yl) | Me | SO₂Me | CF₃ | |
| 2-19 | N | CH₂CMeOMe | Me | SO₂Me | CF₃ | 11.71 (brs, 1H), 8.07 (d, H), 8.00 (d, 1H), 4.54 (dd, 1H), 4.40 (dd, 1H), 3.78 (m, 1H), 3.44 (s, 3H), 3.16 (s, 3H), 2.76 (s, 3H), 1.14 (d, 3H) |

TABLE 3

Compounds according to the invention of the formula (I) in which A represents N

| No. | B | R | X | Z | Physical data (¹H-NMR, DMSO-d₆, 400 MHz) |
|---|---|---|---|---|---|
| 3-1 | CH | C₂H₄OMe | Me | CF₃ | |
| 3-2 | N | C₂H₄OMe | Me | CF₃ | 10.6 (brs, 1H), 8.17 (d, 1H), 7.68 (d, 1H), 4.69 (t, 2H), 3.85 (t, 2H), 3.36 (s, 3H), 2.84 (s, 3H) |
| 3-3 | N | C₂H₄OMe | iPr | CF₃ | |
| 3-4 | CH | C₂H₄OMe | CH₂OMe | CF₃ | |
| 3-5 | N | C₂H₄OMe | CH₂OMe | CF₃ | 11.8 (brs, 1H), 8.34 (d, 1H), 8.02 (d, 1H), 4.78 (s, 2H), 4.51 (t, 2H), 3.77 (t, 2H), 3.28 (s, 3H), 3.23 (s, 3H) |
| 3-6 | N | C₂H₄OMe | CH₂OEt | CF₃ | |
| 3-7 | N | C₂H₄OMe | CH₂OiPr | CF₃ | |
| 3-8 | CH | C₂H₄OMe | CH₂O(CH₂)₂OMe | CF₃ | |
| 3-9 | N | C₂H₄OMe | CH₂O(CH₂)₂OMe | CF₃ | |
| 3-10 | N | C₂H₄OMe | CH₂O(CH₂)₃OMe | CF₃ | |
| 3-11 | N | C₂H₄OMe | CH₂OCH₂CF₃ | CF₃ | |
| 3-12 | N | C₂H₄OMe | CH₂OCH₂cPr | CF₃ | |
| 3-13 | N | C₂H₄OMe | CH₂(3-Me-imidazolin-2-on-1-yl) | CF₃ | |
| 3-14 | N | C₂H₄OMe | CH₂(3-methoxy-4-methyl-1,2,4-triazolin-5-on-1-yl) | CF₃ | 12.17 (brs, 1H), 8.24 (d, 1H), 7.77 (d, 1H), 5.28 (s, 2H), 4.73 (t, 2H), 4.05 (s, 3H), 3.78 (t, 2H), 3.27 (s, 3H), 3.12 (s, 3H) |
| 3-15 | N | C₂H₄OMe | CH₂SMe | CF₃ | |
| 3-16 | CH | C₂H₄OMe | Cl | CF₃ | |
| 3-17 | N | C₂H₄OMe | Cl | CF₃ | 11.99 (brs, 1H), 8.55 (brs, 1H), 8.20 (brs, 1H), 4.37 (m, 2H), 3.72 (m, 2H), 2.39 (s, 3H) |
| 3-18 | N | C₂H₄OMe | Br | CF₃ | |
| 3-19 | N | C₂H₄OMe | Br | CF₃ | |
| 3-20 | N | C₂H₄OMe | SMe | CF₃ | 8.37 (d, 1H), 7.62 (d, 1H), 4.59 (m, 2H), 3.78 (m, 2H), 3.23 (s, 3H), |
| 3-21 | N | C₂H₄OMe | F | F | |
| 3-22 | N | C₂H₄OMe | F | F | |
| 3-23 | CH | C₂H₄OMe | Cl | Cl | |
| 3-24 | N | C₂H₄OMe | Cl | Cl | 9.95 (bs, 1H), 8.16 (d, 1H), 7.46 (d, 1H), 4.61 (t, 2H), 3.83 (t, 2H), 3.39 (s, 3H) |
| 3-25 | CH | C₂H₄OMe | Me | Cl | |
| 3-26 | N | C₂H₄OMe | Me | Cl | |
| 3-27 | N | C₂H₄OMe | SMe | Cl | |
| 3-28 | N | C₂H₄OMe | SO₂Me | Cl | |
| 3-29 | CH | C₂H₄OMe | Cl | SMe | |
| 3-30 | N | C₂H₄OMe | Cl | SMe | |
| 3-31 | CH | C₂H₄OMe | Me | SO₂Me | |
| 3-32 | N | C₂H₄OMe | Me | SO₂Me | |
| 3-33 | N | C₂H₄OMe | SMe | SMe | |
| 3-34 | N | C₂H₄OMe | SO₂Me | SO₂Me | |

B. FORMULATION EXAMPLES a) A dust is obtained by mixing 10 parts by weight of a compound of the formula (I) and/or a salt thereof and 90 parts by weight of talc as inert substance and comminuting the mixture in a hammer mill.

b) A wettable powder which is readily dispersible in water is obtained by mixing 25 parts by weight of a compound of the formula (I) and/or a salt thereof, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A readily water-dispersible dispersion concentrate is obtained by mixing 20 parts by weight of a compound of the formula (I) and/or a salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I) and/or a salt thereof, 75 parts by weight of cyclohexanone as solvent and 10 parts by weight of oxethylated nonylphenol as emulsifier.

e) Water-dispersible granules are obtained by mixing
75 parts by weight of a compound of the formula (I) and/or a salt thereof,
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spraying on water as granulating liquid.

f) Water-dispersible granules are also obtained by homogenizing and precomminuting, in a colloid mill,
25 parts by weight of a compound of the formula (I) and/or a salt thereof,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill and atomizing and drying the resulting suspension in a spray tower by means of a single-substance nozzle.

C. BIOLOGICAL EXAMPLES

1. Pre-Emergence Herbicidal Action Against Harmful Plants

Seeds of monocotyledonous or dicotyledonous weed plants or crop plants are planted in wood-fiber pots in sandy loam and covered with soil. The compounds according to the invention, formulated in the form of wettable powders (WP) or emulsion concentrates (EC), are then applied as aqueous suspension or emulsion at a water application rate of 600 to 800 l/ha (converted) with the addition of 0.2% of wetting agent to the surface of the covering soil. After the treatment, the pots are placed in a greenhouse and kept under good growth conditions for the test plants. The visual assessment of the damage to the test plants is carried out after a trial period of 3 weeks by comparison with untreated controls (herbicidal activity in percent (%): 100% activity=the plants have died, 0% activity=like control plants). Here, for example, the compounds Nos. 1-16, 1-44, 1-60, 1-125, 1-154, 1-162, 1-163, 1-174, 1-187, 1-191, 1-197, 1-200, 1-204, 1-215, 1-245, 1-246, 1-248, 1-343, 1-345, 1-361, 1-366, 1-368, 1-417, 1-450, 1-452, 1-453, 1-456, 1-458, 1-460, 1-463, 1-464, 1-465, 1-468, 1-475, 1-476, 1-488, 1-494, 1-517, 1-572, 1-583, 2-2, 2-4, 2-5, 2-6, 2-7, 2-19, 3-2 and 3-16 each show, at an application rate of 320 g/ha, an activity of at least 90% against *Abutilon theophrasti, Amaranthus retroflexus, Matricara inodora, Stellaria media, Veronica persica* and *Viola tricolor.*

2. Post-Emergence Herbicidal Action Against Harmful Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention, formulated in the form of wettable powders (WP) or emulsion concentrates (EC), are then sprayed as aqueous suspension or emulsion at a water application rate of 600 to 800 l/ha (converted) with the addition of 0.2% of wetting agent onto the green parts of the plants. After the test plants have been kept in the greenhouse under optimum growth conditions for about 3 weeks, the activity of the preparations is rated visually in comparison to untreated controls (herbicidal activity in percent (%): 100% activity=the plants have died, 0% activity=like control plants). Here, for example, the compounds Nos. 1-23, 1-44, 1-125, 1-128, 1-154, 1-157, 1-162, 1-188, 1-197, 1-200, 1-215, 1-220, 1-245, 1-246, 1-344, 1-345, 1-350, 1-366, 1-368, 1-417, 1-450, 1-453, 1-456, 1-460, 1-465, 1-468, 1-475, 1-487, 1-488, 1-494, 1-517, 1-518, 1-583, 2-2, 2-4, 2-5, 2-6, 2-19, 3-2, 3-5 and 3-23 each show, at an application rate of 80 g/ha, an activity of at least 90% against *Abutilon theophrasti, Matricara inodora, Pharbitis purpureum, Stellaria media, Veronica persica* and *Viola tricolor.*

The invention claimed is:

1. An N-(tetrazol-5-yl)- or N-(triazol-5-yl)arylcarboxamide of formula (I) and/or a salt thereof

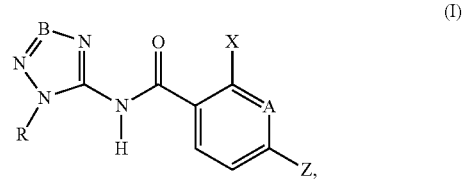

(I)

in which

A represents N or CY,

B represents N or CH,

X represents nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkyl-heteroaryl, ($C_1$-$C_6$)-alkyl-heterocyclyl, where the two last-mentioned radicals are each substituted by s radicals halogen, ($C_1$-$C_6$)-alkyl, halo-($C_1$-$C_6$)-alkyl, $S(O)_n$—($C_1$-$C_6$)-alkyl, ($C_1$-$C_6$)-alkoxy, halo-($C_1$-$C_6$)-alkoxy, and where heterocyclyl carries n oxo groups, Y represents hydrogen, nitro, halogen, cyano, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, ($C_3$-$C_6$)-cycloalkenyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, ($C_1$-$C_6$)-alkyl-$S(O)_nR^2$, ($C_1$-$C_6$)-alkyl-$OR^1$, ($C_1$-$C_6$)-alkyl-$OCOR^1$, ($C_1$-$C_6$)-alkyl-$OSO2R^2$, ($C_1$-$C_6$)-alkyl-$CO_2R^1$, ($C_1$-$C_6$)-alkyl-CN, ($C_1$-$C_6$)-alkyl-$SO_2OR^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$, ($C_1$-$C_6$)-alkyl-$NR^1SO_2R^2$, $N(R^1)_2$, $P(O)(OR^5)_2$, $CH_2P(O)(OR^5)_2$, ($C_1$-$C_6$)-alkyl-phenyl, ($C_1$-$C_6$)-alkyl-heteroaryl, ($C_1$-$C_6$)-alkyl-heterocyclyl, phenyl, heteroaryl or heterocyclyl, where the 6 last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, $S(O)_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl and cyanomethyl, and where heterocyclyl carries n oxo groups, Z represents halogen, cyano, thiocyanato, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, ($C_1$-$C_6$)-alkyl-$S(O)_nR^2$, ($C_1$-$C_6$)-alkyl-$OR^1$, ($C_1$-$C_6$)-alkyl-$OCOR^1$, ($C_1$-$C_6$)-alkyl-$OSO_2R^2$, ($C_1$-$C_6$)-alkyl-$CO_2R^1$, ($C_1$-$C_6$)-alkyl-$SO_2OR^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$, ($C_1$-$C_6$)-alkyl-$NR^1SO_2R^2$, $N(R^1)_2$, $P(O)(OR^5)_2$, heteroaryl, heterocyclyl or phenyl, where the three last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, $S(O)_n$—($C_1$-$C_6$)-alkyl, ($C_1$-$C_6$)-alkoxy and halo-($C_1$-$C_6$)-alkoxy, and where heterocyclyl carries n oxo groups, or Z optionally represents hydrogen, ($C_1$-$C_6$)-alkyl or ($C_1$-$C_6$)-alkoxy if Y represents the radical $S(O)_nR^2$, R represents $CH_2R^6$, $CH_2$-heterocyclyl which is substituted by m oxo groups, ($C_3$-$C_7$)-cycloalkyl which is substituted by t ($C_1$-$C_6$)-alkyl groups, or ($C_2$-$C_6$)-alkyl, ($C_3$-$C_7$)-cycloalkyl, halo-($C_2$-$C_6$)-alkyl, ($C_2$-$C_6$)-alkenyl, halo-($C_2$-$C_6$)-alkenyl, ($C_2$-$C_6$)-alkynyl or halo-($C_2$-$C_6$)-alkynyl, each of which is substituted by u radicals from the group consisting of nitro, cyano, hydroxy, oxo, $SiR^5_3$, $PO(OR^5)_2$, $S(O)_n$—($C_1$-$C_6$)-alkyl, ($C_1$-$C_6$)-alkoxy, halo-($C_1$-$C_6$)-alkoxy, $N(R^3)_2$, $COR^3$, $OCOR^3$, $NR^3COR^3$, $NR^3SO_2R^4$, ($C_3$-$C_6$)-cycloalkyl, heteroaryl, heterocyclyl, phenyl, Q-heteroaryl, Q-heterocyclyl, Q-phenyl and Q-benzyl, where the radicals ($C_3$-$C_6$)-cycloalkyl, heteroaryl, heterocyclyl, phenyl, Q-heteroaryl, Q-heterocyclyl, Q-phenyl and Q-benzyl are each substituted by s substituents from the group consisting of methyl, ethyl, methoxy, cyano, nitro, trifluoromethyl and halogen, and where heterocyclyl and cycloalkyl carry n oxo groups, Q represents O, S or $NR^3$, $R^1$ represents hydrogen, ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_6$)-cycloalkyl, ($C_3$-$C_6$)-cycloalkenyl, ($C_3$-$C_6$)-halocycloalkyl, ($C_1$-$C_6$)-alkyl-O-($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkyl-heteroaryl, heterocyclyl, ($C_1$-$C_6$)-alkyl-heterocyclyl, ($C_1$-$C_6$)-alkyl-O-heteroaryl, ($C_1$-$C_6$)-alkyl-O-heterocyclyl, ($C_1$-$C_6$)-alkyl-$NR^3$-heteroaryl, ($C_1$-$C_6$)-alkyl-$NR^3$-heterocyclyl, where the 21 last-mentioned radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and ($C_1$-$C_4$)-alkoxy-($C_2$-$C_6$)-alkoxycarbonyl, and where heterocyclyl carries n oxo groups, $R^2$ represents ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_6$)-cycloalkyl, ($C_3$-$C_6$)-cycloalkenyl, ($C_3$-$C_6$)-halocycloalkyl, ($C_1$-$C_6$)-alkyl-O-($C_1$-$C_6$)-alkyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkyl-heteroaryl, heterocyclyl, ($C_1$-$C_6$)-alkyl-heterocyclyl, ($C_1$-$C_6$)-alkyl-O-heteroaryl, ($C_1$-$C_6$)-alkyl-O-heterocyclyl, ($C_1$-$C_6$)-alkyl-$NR^3$-heteroaryl, ($C_1$-$C_6$)-alkyl-$NR^3$-heterocyclyl, where the 21 last-mentioned radicals are substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and ($C_1$-$C_4$)-alkoxy-($C_2$-$C_6$)-alkoxycarbonyl, and where heterocyclyl carries n oxo groups, $R^3$ represents hydrogen, ($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, $R^4$ represents ($C_1$-$C_6$)-alkyl, ($C_2$-$C_6$)-alkenyl or ($C_2$-$C_6$)-alkynyl, ($C_3$-$C_6$)-cycloalkyl or ($C_3$-$C_6$)-cycloalkyl-($C_1$-$C_6$)-alkyl, $R^5$ represents ($C_1$-$C_4$)-alkyl, $R^6$ represents $OCOOR^4$, $NR^4COOR^4$, $S(O)_n$—($C_1$-$C_6$)-alkyl, $S(O)_n$—($C_1$-$C_6$)-haloalkyl, nitro, cyano, $SiR^5_3$, $PO(OR^5)_2$, heterocyclyl or cycloalkyl, where the two last-mentioned radicals carry m oxo or hydroxy groups, m represents 1 or 2, n represents 0, 1 or 2, s represents 0, 1, 2 or 3, t represents 1, 2, 3 or 4, and u represents 1, 2, 3, 4 or 5.

2. The N-(tetrazol-5-yl)- or N-(triazol-5-yl)arylcarboxamide and/or salt as claimed in claim 1 in which A represents N or CY, B represents N or CH, X represents nitro, halogen, cyano, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_6$)-cycloalkyl, halo-($C_3$-$C_6$)-cycloalkyl, ($C_1$-$C_6$)-alkyl-O-($C_1$-$C_6$)-alkyl, ($C_3$-$C_6$)-cycloalkyl-($C_1$-$C_6$)-alkyl, halo-($C_3$-$C_6$)-cycloalkyl-($C_1$-$C_6$)-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, ($C_1$-$C_6$)-alkyl-$S(O)_nR^2$, ($C_1$-$C_6$)-alkyl-$OR^1$, ($C_1$-$C_6$)-alkyl-$OCOR^1$, ($C_1$-$C_6$)-alkyl-$OSO_2R^2$, ($C_1$-$C_6$)-alkyl-$CO_2R^1$, ($C_1$-$C_6$)-alkyl-$SO_2OR^1$, ($C_1$-$C_6$)-alkyl-$CON(R^1)_2$, ($C_1$-$C_6$)-alkyl-$SO_2N(R^1)_2$, ($C_1$-$C_6$)-alkyl-$NR^1COR^1$ or ($C_1$-$C_6$)-alkyl- NR$^1$SO$_2$R$^2$, (C$_1$-C$_6$)-alkyl-heteroaryl, (C$_1$-C$_6$)-alkyl-heterocyclyl, where the two last-mentioned radicals are each substituted by s radicals halogen, (C$_1$-C$_6$)-alkyl, halo-(C$_1$-C$_6$)-alkyl, S(O)$_n$—(C$_1$-C$_6$)-alkyl, (C$_1$-C$_6$)-alkoxy, halo-(C$_1$-C$_6$)-alkoxy, and where heterocyclyl carries n oxo groups, Y represents hydrogen, nitro, halogen, cyano, thiocyanato, (C$_1$-C$_6$)-alkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_3$-C$_6$)-alkynyl, (C$_3$-C$_6$)-cycloalkyl, (C$_3$-C$_6$)-cycloalkenyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, COR$^1$, OR$^1$, COOR$^1$, OSO$_2$R$^2$, S(O)$_n$R$^2$, SO$_2$OR$^1$, SO$_2$N(R$^1$)$_2$, N(R$^1$)$_2$, NR$^1$SO$_2$R$^2$, NR$^1$COR$^1$, (C$_1$-C$_6$)-alkyl-S(O)$_n$R$^2$, (C$_1$-C$_6$)-alkyl-OR$^1$, (C$_1$-C$_6$)-alkyl-OCOR$^1$, (C$_1$-C$_6$)-alkyl-OSO$_2$R$^2$, (C$_1$-C$_6$)-alkyl-CO$_2$R$^1$, (C$_1$-C$_6$)-alkyl-SO$_2$OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, (C$_1$-C$_6$)-alkyl-phenyl, (C$_1$-C$_6$)-alkyl-heteroaryl, (C$_1$-C$_6$)-alkyl-heterocyclyl, phenyl, heteroaryl or heterocyclyl, where the 6 last-mentioned radicals are each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy, (C$_1$-C$_6$)-alkoxy-(C$_1$-C$_4$)-alkyl and cyanomethyl, and where heterocyclyl carries n oxo groups, Z represents halogen, cyano, thiocyanato, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_3$-C$_6$)-alkynyl, (C$_3$-C$_6$)-cycloalkyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, COR$^1$, COOR$^1$, C(O)N(R$^1$)$_2$, C(O)NR$^1$OR$^1$, OSO$_2$R$^2$, S(O)$_n$R$^2$, SO$_2$OR$^1$, SO$_2$N(R$^1$)$_2$, NR$^1$SO$_2$R$^2$, NR$^1$COR$^1$, (C$_1$-C$_6$)-alkyl-S(O)$_n$R$^2$, (C$_1$-C$_6$)-alkyl-OR$^1$, (C$_1$-C$_6$)-alkyl-OCOR$^1$, (C$_1$-C$_6$)-alkyl-OSO$_2$R$^2$, (C$_1$-C$_6$)-alkyl-CO$_2$R$^1$, (C$_1$-C$_6$)-alkyl-SO$_2$OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, 1,2,4-triazol-1-yl, or Z optionally represents hydrogen, (C$_1$-C$_6$)-alkyl or (C$_1$-C$_6$)-alkoxy if Y represents the radical S(O)$_n$R$^2$, R represents CH$_2$R$^6$, CH$_2$-heterocyclyl which is substituted by m oxo groups, or (C$_2$-C$_6$)-alkyl, (C$_3$-C$_7$)-cycloalkyl, halo-(C$_2$-C$_6$)-alkyl, (C$_2$-C$_6$)-alkenyl, halo-(C$_2$-C$_6$)-alkenyl, (C$_2$-C$_6$)-alkynyl or halo-(C$_2$-C$_6$)-alkynyl, each of which is substituted by u radicals from the group consisting of nitro, cyano, hydroxy, oxo, SiR$^5$$_3$, PO(OR$^5$)$_2$, S(O)$_n$—(C$_1$-C$_6$)-alkyl, (C$_1$-C$_6$)-alkoxy, halo-(C$_1$-C$_6$)-alkoxy, N(R$^3$)$_2$, COR$^3$, OCOR$^3$, NR$^3$COR$^3$, NR$^3$SO$_2$R$^4$, (C$_3$-C$_6$)-cycloalkyl, heteroaryl, heterocyclyl, phenyl, Q-heteroaryl, Q-heterocyclyl, Q-phenyl and Q-benzyl, where the radicals (C$_3$-C$_6$)-cycloalkyl, heteroaryl, heterocyclyl, phenyl, Q-heteroaryl, Q-heterocyclyl, Q-phenyl and Q-benzyl are each substituted by s substituents from the group consisting of methyl, ethyl, methoxy, cyano, nitro, trifluoromethyl and halogen, and where heterocyclyl and cycloalkyl carry n oxo groups, Q represents O, S or NR$^3$, R$^1$ represents hydrogen, (C$_1$-C$_6$)-alkyl, (C$_2$-C$_6$)-alkenyl, (C$_2$-C$_6$)-alkynyl, (C$_3$-C$_6$)-cycloalkyl, (C$_3$-C$_6$)-cycloalkyl-(C$_1$-C$_6$)-alkyl, (C$_1$-C$_6$)-alkyl-O-(C$_1$-C$_6$)-alkyl, phenyl, phenyl-(C$_1$-C$_6$)-alkyl, heteroaryl, (C$_1$-C$_6$)-alkyl-heteroaryl, heterocyclyl, (C$_1$-C$_6$)-alkyl-heterocyclyl, (C$_1$-C$_6$)-alkyl-O-heteroaryl, (C$_1$-C$_6$)-alkyl-O-heterocyclyl, (C$_1$-C$_6$)-alkyl-NR$^3$-heteroaryl or (C$_1$-C$_6$)-alkyl-NR$^3$-heterocyclyl, where the 16 last-mentioned radicals are substituted by s radicals from the group consisting of cyano, halogen, nitro, OR$^3$, S(O)$_n$R$^4$, N(R$^3$)$_2$, NR$^3$OR$^3$, COR$^3$, OCOR$^3$, NR$^3$COR$^3$, NR$^3$SO$_2$R$^4$, CO$_2$R$^3$, CON(R$^3$)$_2$ and (C$_1$-C$_4$)-alkoxy-(C$_2$-C$_6$)-alkoxycarbonyl, and where heterocyclyl carries n oxo groups, R$^2$ represents (C$_1$-C$_6$)-alkyl, (C$_2$-C$_6$)-alkenyl, (C$_2$-C$_6$)-alkynyl, (C$_3$-C$_6$)-cycloalkyl, (C$_3$-C$_6$)-cycloalkyl-(C$_1$-C$_6$)-alkyl, (C$_1$-C$_6$)-alkyl-O-(C$_1$-C$_6$)-alkyl, phenyl, phenyl-(C$_1$-C$_6$)-alkyl, heteroaryl, (C$_1$-C$_6$)-alkyl-heteroaryl, heterocyclyl, (C$_1$C$_6$)-alkyl-heterocyclyl, (C$_1$-C$_6$)-alkyl-O-heteroaryl, (C$_1$-C$_6$)-alkyl-O-heterocyclyl, (C$_1$-C$_6$)-alkyl-NR$^3$-heteroaryl or (C$_1$-C$_6$)-alkyl-NR$^3$-heterocyclyl, where these radicals are substituted by s radicals from the group consisting of cyano, halogen, nitro, OR$^3$, S(O)$_n$R$^4$, N(R$^3$)$_2$, NR$^3$OR$^3$, NR$^3$SO$_2$R$^4$, COR$^3$, OCOR$^3$, NR$^3$COR$^3$, CO$_2$R$^3$, CON(R$^3$)$_2$ and (C$_1$-C$_4$)-alkoxy-(C$_2$-C$_6$)-alkoxycarbonyl, and where heterocyclyl carries n oxo groups, R$^3$ represents hydrogen, (C$_1$-C$_6$)-alkyl, (C$_2$-C$_6$)-alkenyl, (C$_2$-C$_6$)-alkynyl, (C$_3$-C$_6$)-cycloalkyl or (C$_3$-C$_6$)-cycloalkyl-(C$_1$-C$_6$)-alkyl, R$^4$ represents (C$_1$-C$_6$)-alkyl, (C$_2$-C$_6$)-alkenyl or (C$_2$-C$_6$)-alkynyl, R$^5$ represents methyl or ethyl, R$^6$ represents OCOOR$^4$, NR$^4$COOR$^4$, S(O)$_n$—(C$_1$-C$_6$)-alkyl, S(O)$_n$—(C$_1$-C$_6$)-haloalkyl, nitro, cyano, SiR$^5$$_3$, PO(OR$^5$)$_2$ or heterocyclyl which carries m oxo groups, m represents 1 or 2, n represents 0, 1 or 2, s represents 0, 1, 2 or 3, and u represents 1, 2, 3, 4 or 5.

3. The N-(tetrazol-5-yl)- or N-(triazol-5-yl)arylcarboxamide and/or salt thereof as claimed in claim 1 in which A represents N or CY, B represents N or CH, X represents nitro, halogen, cyano, (C$_1$-C$_6$)-alkyl, halo-(C$_1$-C$_6$)-alkyl, (C$_3$-C$_6$)-cycloalkyl, OR$^1$, S(O)$_n$R$^2$, (C$_1$-C$_6$)-alkyl-S(O)$_n$R$^2$, (C$_1$-C$_6$)-alkyl-OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, (C$_1$-C$_6$)-alkyl-heteroaryl, (C$_1$-C$_6$)-alkyl-heterocyclyl, where the two last-mentioned radicals are each substituted by s radicals halogen, (C$_1$-C$_6$)-alkyl, halo-(C$_1$-C$_6$)-alkyl, S(O)$_n$—(C$_1$-C$_6$)-alkyl, (C$_1$-C$_6$)-alkoxy, halo-(C$_1$-C$_6$)-alkoxy, and where heterocyclyl carries n oxo groups, Y represents hydrogen, nitro, halogen, cyano, (C$_1$-C$_6$)-alkyl, (C$_1$-C$_6$)-haloalkyl, OR$^1$, S(O)$_n$R$^2$, SO$_2$N(R$^1$)$_2$, N(R$^1$)$_2$, NR$^1$SO$_2$R$^2$, NR$^1$COR$^1$, (C$_1$-C$_6$)-alkyl-S(O)$_n$R$^2$, (C$_1$-C$_6$)-alkyl-OR$^1$, (C$_1$-C$_6$)-alkyl-CON(R$^1$)$_2$, (C$_1$-C$_6$)-alkyl-SO$_2$N(R$^1$)$_2$, (C$_1$-C$_6$)-alkyl-NR$^1$COR$^1$, (C$_1$-C$_6$)-alkyl-NR$^1$SO$_2$R$^2$, (C$_1$-C$_6$)-alkyl-phenyl, (C$_1$-C$_6$)-alkyl-heteroaryl, (C$_1$-C$_6$)-alkyl-heterocyclyl, phenyl, heteroaryl or heterocyclyl, where the 6 last-mentioned radicals are each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy, (C$_1$-C$_6$)-alkoxy-(C$_1$-C$_4$)-alkyl and cyanomethyl, and where heterocyclyl carries n oxo groups, Z represents halogen, cyano, halo-(C$_1$-C$_6$)-alkyl, (C$_3$-C$_6$)-cycloalkyl, S(O)$_n$R$^2$, 1,2,4-triazol-1-yl, or Z optionally represents hydrogen, methyl, methoxy or ethoxy if Y represents the radical S(O)$_n$R$^2$, R represents CH$_2$R$^6$, CH$_2$-heterocyclyl, where heterocyclyl carries m oxo groups, or (C$_2$-C$_6$)-alkyl, (C$_3$-C$_7$)- cycloalkyl, halo-$(C_2-C_6)$-alkyl, $(C_2-C_6)$-alkenyl, halo-$(C_2-C_6)$-alkenyl, $(C_2-C_6)$-alkynyl or halo-$(C_2-C_6)$-alkynyl, each of which is substituted by u radicals from the group consisting of nitro, cyano, hydroxy, oxo, $SiR^5_3$, $PO(OR^5)_2$, $S(O)_n-(C_1-C_6)$-alkyl, $(C_1-C_6)$-alkoxy, halo-$(C_1-C_6)$-alkoxy, $N(R^3)_2$, $COR^3$, $OCOR^3$, $NR^3COR^3$, $NR^3SO_2R^4$, $(C_3-C_6)$-cycloalkyl, heteroaryl, heterocyclyl, phenyl, Q-heteroaryl, Q-heterocyclyl, Q-phenyl and Q-benzyl, where the radicals $(C_3-C_6)$-cycloalkyl, heteroaryl, heterocyclyl, phenyl, Q-heteroaryl, Q-heterocyclyl, Q-phenyl and Q-benzyl are each substituted by s substituents from the group consisting of methyl, ethyl, methoxy, cyano, nitro, trifluoromethyl and halogen, and where heterocyclyl and cycloalkyl carry n oxo groups, Q represents O, S or $NR^3$, $R^1$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, $(C_1-C_6)$-alkyl-O-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl or $(C_1-C_6)$-alkyl-$NR^3$-heterocyclyl, where the 16 last-mentioned radicals are substituted by s radicals from the group consisting of cyano, halogen, nitro, $OR^3$, $S(O)_nR^4$, $N(R^3)_2$, $NR^3OR^3$, $COR^3$, $OCOR^3$, $NR^3COR^3$, $NR^3SO_2R^4$, $CO_2R^3$, $CON(R^3)_2$ and $(C_1-C_4)$-alkoxy-$(C_2-C_6)$-alkoxycarbonyl, and where heterocyclyl carries n oxo groups, $R^2$ represents $(C_1-C_6)$-alkyl, $(C_3-C_6)$-cycloalkyl or $(C_3-C_6)$-cycloalkyl-$(C_1-C_6)$-alkyl, where the three radicals mentioned above are each substituted by s radicals from the group consisting of halogen and $OR^3$, $R^3$ represents hydrogen or $(C_1-C_6)$-alkyl, $R^4$ represents $(C_1-C_6)$-alkyl, $R^5$ represents methyl or ethyl, $R^6$ represents $OCOOR^4$, $NR^4COOR^4$, $S(O)_n-(C_1-C_6)$-alkyl, $S(O)_n-(C_1-C_6)$-haloalkyl, nitro, cyano, $SiR^5_3$, $PO(OR^5)_2$, m represents 1 or 2, n represents 0, 1 or 2, s represents 0, 1, 2 or 3, and u represents 1, 2, 3, 4 or 5.

4. A herbicidal composition comprising a herbicidally effective amount of at least one compound as claimed in claim 1.

5. The herbicidal composition as claimed in claim 4 in a mixture with at least one formulation auxiliary.

6. The herbicidal composition as claimed in claim 4, comprising at least one further pesticidally active compound selected from the group consisting of insecticides, acaricides, herbicides, fungicides, safeners, and growth regulators.

7. The herbicidal composition as claimed in claim 6, comprising a safener.

8. The herbicidal composition as claimed in claim 7, comprising cyprosulfamid, cloquintocet-mexyl, mefenpyr-diethyl and/or isoxadifen-ethyl.

9. The herbicidal composition as claimed in claim 6, comprising a further herbicide.

10. A method for controlling unwanted vegetation, comprising applying an effective amount of at least one compound as claimed in claim 1 to a plant and/or a site of unwanted vegetation.

11. A compound as claimed in claim 1 capable of being used for controlling an unwanted plant.

12. A compound as claimed in claim 11, wherein the compound is capable of being used for controlling an unwanted plant in a crop of a useful plant.

13. A compound as claimed in claim 12, wherein the useful plant comprises a transgenic useful plant.

14. A method for controlling unwanted vegetation, comprising applying an effective amount of a herbicidal composition as claimed in claim 4 to a plant and/or site of unwanted vegetation.

15. A herbicidal composition as claimed in claim 4, capable of being used for controlling an unwanted plant.

* * * * *